United States Patent
Bianchi et al.

(10) Patent No.: US 9,943,528 B2
(45) Date of Patent: Apr. 17, 2018

(54) NON-BIOCONVERTIBLE $C_3$-SUBSTITUTED PREGNENOLONE DERIVATIVES FOR USE IN THE TREATMENT OF TREATMENT-RESISTANT DEPRESSION

(71) Applicant: MAPREG, Le Kremlin Bicêtre (FR)

(72) Inventors: Massimiliano Bianchi, Dublin (IE); Etienne Baulieu, Paris (FR); Isabelle Villey, Colombes (FR)

(73) Assignee: MAPREG, Le Kremlin Bicêtre (FR)

( * ) Notice: Subject to any disclaimer, the term of this patent is extended or adjusted under 35 U.S.C. 154(b) by 0 days.

(21) Appl. No.: 15/444,778

(22) Filed: Feb. 28, 2017

(65) Prior Publication Data

US 2017/0252358 A1   Sep. 7, 2017

Related U.S. Application Data

(60) Provisional application No. 62/301,869, filed on Mar. 1, 2016.

(51) Int. Cl.
*A61K 31/57* (2006.01)
(52) U.S. Cl.
CPC ..................... *A61K 31/57* (2013.01)
(58) Field of Classification Search
CPC ....................................................... A61K 31/57
See application file for complete search history.

(56) References Cited

U.S. PATENT DOCUMENTS 8,334,278 B2   12/2012   Baulieu et al.

FOREIGN PATENT DOCUMENTS

WO   WO 2004/067010 A1   8/2004

OTHER PUBLICATIONS

Akinfiresoye, et al. "Antidepressant Effects of AMPA and Ketamine Combination: Role of Hippocampal BDNF, Synapsin, and mTOR," *Psychopharm.*, 230:1-21, (2013).
Alonso, et al. "Use of Mental Health Services in Europe: Results From the European Study of the Epidemiology of Mental Disorders (ESEMeD) Project," *Acta. Psychiatrica Scand.*, 109:47-54, (2004).
Alonso, et al. "Disability and Quality of Life Impact of Mental Disorders in Europe: Results From the European Study of the Epidemiology of Mental Disorders (ESEMeD) Project," *Acta. Psychiatrica Scand.*, 109:38-46, (2004).
Andlin-Sobocki, et al. "Cost of Affective Disorders in Europe," *Euro. Jour. Neurol.*, 12:34-38, (2005).
Armario, et al. "Comparison of the Behavioural and Endocrine Response to Forced Swimming Stress in Five Inbred Strains of Rats," *Psychoneuro.*, 20:879-890, (1995).
Berman, et al. "Antidepressant Effects of Ketamine in Depressed Patients," *Biol Psych.*, 47:351-354, (2000).
Bianchi, et al. "3β-Methoxy-Pregnenolone (MAP4343) as an Innovative Therapeutic Approach for Depressive Disorders," *PNAS*, 109:1713-1718, (2012).
Bianchi, et al. "3β-Methoxy-Pregnenolone Exerts Antidepressant Efficacy in 'Depressed' Wistar-Kyoto Rats and in Aged Wistar Rats," *Transpharmation Ireland Limited, Trinity College Institute of Neuroscience*, (2015).
Browne, et al. "Antidepressant-Like Effects of Buprenorphine in Rats Are Strain Dependent," *Behav. Brain Res.*, 278:385-392, (2015).
Carr, et al. "Antidepressant-Like Effects of κ-Opioid Receptor Antagonists in Wistar Kyoto Rats," *Neuropsych.*, 35:752-763, (2010).
Cominski, et al. "The Role of the Hippocampus in Avoidance Learning and Anxiety Vulnerability," *Front. Behav. Neurosci.*, 8:1-10, (2014).
Druss, et al. "Health and Disability Costs of Depressive Illness in a Major U.S. Corporation," *Am J Psychiatry*, 1578:1274-1278, (2000).
Dugovic, et al. "Sleep in the Wistar-Kyoto Rat, A Putative Genetic Animal Model for Depression," *NeuroReport*, 3:1-5, (2000).
Durand, et al. "Effects of Repeated Fluoxetine on Anxiety-Related Behaviours, Central Serotonergic Systems, and the Corticotropic Axis in SHR and WKY Rats," *Neuropharma.* 38:893-901, (1999).
Durand, et al. "Wistar-Kyoto Rats are Sensitive to the Hypolocomotor and Anxiogenic Effects of mCPP," *Behav. Pharmacol.*, 14:173-177, (2003).
Ennaceur, et al. "A New One-Trial Test for Neurobiological Studies of Memory in Rats. 1: Behavioral Data," *Behav. Brain. Res.*, 31:47-59, (1988).
Fava, et al. "Definition and Epidemiology of Treatment-Resistant Depression," *Psychia. Clin. North Am.*, 19:179-200, (1996).
Ferguson, et al. "A Longitudinal Study of Short- and Long-Term Activity Level in Male and Female Spontaneously Hypertensive, Wistar-Kyoto, and Sprague-Dawley Rats," *Behav. Neurosci.*, 117:271-282, (2003).
Ferguson, et al. "Early Behavioral Development in the Spontaneously Hypertensive Rat: A Comparison With the Wistar-Kyoto and Sprague-Dawley Strains," *Behav. Neurosci.*, 117:263-270, (2003).
Fontaine-Leonir, et al. "Microtubule-Associated Protein 2 (MAP2) is a Neurosteroid Receptor," *PNAS*, 103:4711-4716, (2006).
Garcia, et al. "Acute Administration of Ketamine Induces Antidepressant-Like Effects in the Forced Swimming Test and Increases BDNF Levels in the Rat Hippocampus," *Prog. Neuro-Psychopharm & Biol. Psych.*, 32:140-144, (2008).
Greden, "The Burden of Disease for Treatment-Resistant Depression," *J Clin Psych.*, 62:26-31, (2001).

(Continued)

*Primary Examiner* — Sudhakar Katakam
(74) *Attorney, Agent, or Firm* — Arrigo, Lee, Guttman & Mouta-Bellum LLP

(57) ABSTRACT

The present invention relates to methods for the treatment of treatment-resistant depression (TRD), comprising the administration of compounds of formula (I), which are blocked in $C_3$ position and cannot metabolize in vivo into pregnenolone derivatives and which do not have significant affinity for steroid hormonal receptors and for all tested classical main receptors and receptors of neurotransmitters of the central nervous system.

3 Claims, 22 Drawing Sheets
(2 of 22 Drawing Sheet(s) Filed in Color)

(56) References Cited

OTHER PUBLICATIONS

Greenberg, et al. "The Economic Burden of Depression in 1990," *J Clin Psych*, 54:405-418, (1993).
Griebel, et al. "Behavioral Effects of Acute and Chronic Fluoxetine in Wistar-Kyoto Rats," *Physiol. & Behav.*, 67:315-320, (1999).
Hauser, et al. "Alcohol Induced Depressive-Like Behavior is Associated with a Reduction in Hippocampal BDNF," *Pharmacol Biochem Behav.*, 100:253-258, (2011).
Jiao, et al. "Animal Models of Anxiety Vulnerability—The Wistar Kyoto Rat," (2011).
Kessler, et al. "The Epidemiology of Major Depressive Disorder," *JAMA*, 289:3095-3105, (2003).
Lahmame, et al "Are Wistar-Kyoto Rats a Genetic Animal Model of Depression Resistant to Antidepressants," *Euro. Jour. Pharm.*, 337:115-123, (1997).
Little, "Treatment-Resistant Depression," *Amer. Fam. Phys.*, 80:167-172, (2009).
Lopez-Rubalcava, et al. "Strain Differences in the Behavioral Effects of Antidepressant Drugs in the Rat Forced Swimming Test," *Neuropsychopharmacology*, 22:191-198, (2000).
Malkesman, et al. "Assessment of Antidepressant and Anxiolytic Properties of NK1 Antagonists and Substance P in Wistar Kyoto Rats," *Psych & Behav*, 90:619-625, (2007).
Murakami, et al. "Pregnenolone Binds to Microtubule-Associated Protein 2 and Stimulates Microtubule Assembly," *PNAS*, 97:3579-3584, (2000).
McIntyre, et al. "Treatment-Resistant Depression: Definitions, Review of the Evidence, and Algorithmic Approach, *J. Affec. Disord.*," 156:1-7, (2014).
Okamoto, et al. "Development of a Strain of Spontaneously Hypertensive Rats," *Japanese Circ. Jour.*, 27:282-293, (1963).
Pare, et al. "Depressive Behavior and Stress Ulcer in Wistar Kyoto Rats," *J. Phys.*, 87:-229-238, (1993).
Pare, "Open Field, Learned Helplessness, Conditioned Defensive Burying, and Forced-Swim Tests in WKY Rats," *Physiol. & Behav.*, 55:433-439, (1994).
Pare, et al. "Differences in the Stress Response of Wistar-Kyoto (WKY) Rats from Different Vendors," *Physiol. & Behav.*, 62:643-648, (1997).
Paresys, et al. "Effects of the Synthetic Neurosteriod 3β-Methoxypregnenolone (MAP4343) on Behavioral and Physiological Alterations Provoked by Chronic Psychosocial Stress in Tree Shrews," *Intl. Jour. Neuropsychopharm.*, 1-12, (2015).
Pollier, et al. "Serotonin Reuptake Inhibition by Citalopram in Rat Strains Differing for Their Emotionality," *Neuropsychopharma.*, 22:64-76, (2000).
Rush, of al. "STAR*D: Revising Conventional Wisdom," *CNS Drugs*, 8:627-647, (2002).
Scheuing, et al. "Antidepressant Mechanism of Ketamine: Perspective From Preclinical Studies," *Front. Neurosci.*, 9:1-7, (2015).
Scholl, et al. "Central Monoamine Levels Differ Between Rat Strains Used in Studies of Depressive Behavior," *Brain Res.*, 1355:41-51, (2010).
Tejani-Butt, et al. "Strain-Dependent Modification of Behavior Following Antidepressant Treatment," *Prog. Neuro-Psychophatm. & Biol. Psych.*, 27:7-14, (2003).
Thase, et al. "When at First You Don't Succeed: Sequential Strategies for Antidepressant Nonresponders," *J. Clin. Psychiatry*, 58:23-29, (1997).
Tizabi, et al. "Antidepressant-Like Effects of Low Ketamine Dose is Associated With Increased Hippocampal AMPA/NMDA Receptor Density Ratio in Female Wistar-Kyoto Rats," *Neuroscience*, 213:72-80, (2012).
Trivedi, et al. "Clinical Results for Patients With Major Depressive Disorder in the Texas Medication Algorithm Project," *Arch Gen Psychiatry.*, 61:669-680, (2004).
Trivedi, et al. "Use of Treatment Algorithms for Depression," *J. Clin. Psych.*, 67:1458-1465, (2006).
West, "Stereological Methods for Estimating the Total Number of Neurons and Synapses: Issues of Precision and Bias," *TINS*, 22:51-61, (1999).
Will, et al. "Selectively Bred Wistar-Kyoto Rats: An Animal Model of Depression and Hyper-Responsiveness to Antidepressants," *Mol. Psych.*, 8:925-932, (2003).
Willner, et al. "Treatment-Resistant Depression: Are Animal Models of Depression Fit for Purpose," *Psychopharm.*, 232:3473-3495, (2015).
Willner, et al. "Resistance to Antidepressant Drugs: The Case for a More Predisposition-Based and Less Hippocampocentric Research Paradigm," *Behav. Pharm.*, 25:352-371, (2014).
Yilmaz, et al. "Prolonged Effect of an Anesthetic Dose of Ketamine on Behavioral Despair," *Pharma. Biochem. & Behav.*, 71:341-344, (2002).
Zarate, et al. "A Randomized Trial of an N-Methyl-D-Aspartate Antagonist in Treatment-Resistant Major Depression," *Arch Gen Psych.*, 63:856-864, (2006).

NON-BIOCONVERTIBLE C₃-SUBSTITUTED PREGNENOLONE DERIVATIVES FOR USE IN THE TREATMENT OF TREATMENT-RESISTANT DEPRESSION

CROSS-REFERENCE TO RELATED APPLICATIONS

This application claims the benefit of U.S. Provisional Application No. 62/301,869, filed Mar. 1, 2016.

TECHNICAL FIELD OF THE INVENTION

The present invention is in the field of treatment of treatment-resistant depression. It relates to the use of particular derivatives of pregnenolone, which are blocked in $C_3$ position and cannot metabolize in vivo into pregnenolone derivatives and which do not have significant affinity for steroid hormonal receptors and for all tested classical main receptors and receptors of neurotransmitters of the central nervous system, for the treatment of treatment-resistant depression (TRD).

BACKGROUND ART

Affective disorders (anxiety and depression) are the most common psychiatric disorders in the general population (Alonso et al, 2004a; Kessler et al., 2005), considering that approximately 35% of women and 20% of men will present one or the other of these conditions at least once during their life. In the absence of care, they are generally in the form of episodes lasting over at least several months and that may repeat over life. Their impact is variable depending on their severity, but on average it appears as very significant, especially in the professional and social fields (Alonso et al, 2004b; Greden et al., 2001), due to direct medical and medical-social expenses and indirect expenses incurred by work absenteeism. The annual cost of depression in the US is close to that of cardiovascular diseases and is estimated at $44 billion of which nearly 12% are attributable to hospitalizations (Greenberg et al, 1993). In Europe, data is difficult to gather but some studies suggest direct cost per patient of up to € 14,500 and indirect costs of approximately € 4,500, for a total of just over 105 million euros (Andlin-Sopcki & Wittchen, 2005). Depressive illnesses, which often affect young and working populations, also have a significant economic impact on "indirect costs" measured in terms of productivity for the individual and for society (Druss et al, 2000).

There are well validated first-line therapeutic strategies (in general drug and/or psychosocial) for most categories of depressive disorders (DDs), that can effectively treat more than half of patients.

However, if the majority of depressive episodes regress during a first treatment, it is generally accepted that 20% of depressive episodes become chronic and that 30% of all depressions are resistant to conventional antidepressant drugs (Fava and Davidson, 1996). Patients with such treatment-resistant depression (TRD) may maintain intense symptoms for several months or years despite the use of many treatments. There are currently no precise and consensual recommendations for the monitoring and evaluation of patients showing failure to a first antidepressant treatment and a resistant form of depression. In general, practitioners test different classes of antidepressants, combination therapies or the use of other therapeutic methods such as electroconvulsive therapy (ECT) in severe and resistant depressions (Little 2009; Trivedi et al, 2006). While different types of algorithms have been proposed to guide the selection of treatment strategies based on initial responses and have shown some improvement in the efficiency of treatment (Trivedi et al, 2004), there is still a need for true therapies for those depressive patients resistant to conventional antidepressant drugs. This is particularly true because it has been demonstrated that the probability of response to a drug treatment (n=i) decreases significantly depending on the number of drugs tested before (n=2, n=3). Thus, after at least three or four drug trials, the probability of response to the drug is very low (<15%) and the use of other therapeutic options with different biological effects (physical treatments such as ECT therapy) is necessary (Rush et al., 2009).

Presently, treatments that have been found really efficient in treatment-resistant depression are either highly invasive or based on chemical drugs with significant secondary effects:

Electroconvulsive therapy (ECT) has been shown to be efficient in the treatment of treatment-resistant depression (TRD).

However, ECT involves intentionally triggering a brief seizure by passing small electric currents through the brain, under general anesthesia, and it thus a quite invasive procedure that necessitates hospitalization of the patient and high medical skills. In addition, ECT is not devoid of side effects, such as confusion, short-term or sometimes long-term memory losses, nausea, headache, jaw pain or muscle ache. Moreover, during ECT, heart rate and blood pressure increase and this treatment may not be recommended in people with unstable heart problems.

Ketamine has been reported to exert a rapid antidepressant-like efficacy (Scheuing et al., 2015). In particular, ketamine has been shown to decrease immobility in the forced-swimming test (FST) the Wistar Kyoto rat strain (WKY) (Tizabi et al., 2012) and to decrease explicit suicidal ideation in human TRD patients (Scheuing et al., 2015).

However, ketamine is also known to temporarily cause dissociative symptoms, to have risk for abuse, and to increase oxidative stress in the rat brain. Moreover, while ketamine rapidly reduces depressive symptoms, repeated infusions are necessary to maintain its effects over time, the effects of a single infusion only lasting about 1 week. Such repeated infusions may lead to serious side effects, such as cognitive impairments, psychomimetic symptoms, and schizophrenia-like behaviors (Scheuing et al., 2015).

Despite its efficiency in alleviating depressive symptoms in TRD, ketamine cannot thus be widely used in the treatment of TRD.

From the above, it appears that the only treatments available at this stage for the treatment of TRD are not satisfactory, since they are either quite invasive or prone to significant side effects. New treatments of TRD, that would not have these drawbacks, but would instead be non-invasive and well tolerated, without significant side effects, are thus needed.

It has been shown that stress is involved in the onset of depression, primarily by damaging the hippocampus, and most antidepressant drugs have been obtained based on stress-related animal models of depressive disorders and found to have the common mechanism of action of reversing the neurotoxic effects of stress and repairing the damaged hippocampus (Willner & Belzung, 2015).

It is thus not surprising that most antidepressant drugs are not efficient in depressive disorders in which stress is not the main factor involved in the pathology. Indeed, many factors are known to increase vulnerability to depression, including a clinical history of depression and a variety of genetic, personality or developmental risk factors. When such factors are present, the role of stress in depression is correspondingly diminished and the major substrate for most antidepressant action (stress-induced neurotoxicity) is absent or minor. In this context, it should be noted that increased vulnerability to depression has been shown to be associated with resistance to antidepressant drug treatment (Willne et al. 2014).

In fact, treatment-resistant depression appears to be associated to risk factors for depression, which predispose to the precipitation of depressive episodes by relatively low levels of stress.

The above clearly shows that while stress-related animal models of depressive disorders are useful for predict therapeutic efficiency of a compound in depressive disorders precipitated by stress (the most common form of depressive disorder), they are not appropriate to predict therapeutic efficiency of a compound in the treatment of treatment-resistant depression. In this respect, it should be noted that most antidepressant drugs, including SSRIs, have been screened using such stress-related animal models of depressive disorders and were thus found to be efficient in these models. This however did not prevent them to be inefficient in many cases of treatment-resistant depression.

Instead, only animal models that incorporate predisposing factors leading to heightened stress responsiveness may be used for predicting therapeutic efficiency of a compound in the treatment of treatment-resistant depression (TRD). Such models include those proposed in Willner & Belzung, 2015, the 5 better models for this purpose being considered to be the Wistar-Kyoto (WKY) and congenital learned helplessness (cLH) rat strains, the high anxiety behaviour (HAB) mouse strain and the CB1 receptor knockout and OCT2 null mutant mouse strains. These animal models have been shown to display at least some resistance to some conventional antidepressant drugs found inefficient for the treatment of TRD in a clinical setting. For instance, WKY rats have been found to be resistant to acute or chronic administration of fluoxetine (an SSRI, see Durand et al., 1999; Griebel et al., 1999; Lopez-Rubalcava and Lucki, 2000), acute administration of citalopram (another SSRI, see Pollier et al., 2000), as well as for sub-chronic administration (12 days) of paroxetine (a third SSRI, see Tejani-Butt et al., 2003), and may thus be used as an animal model of TRD.

3β-methoxy-pregna-5α-ene-20α-one (also referred to as 3β-methoxy-pregnenolone or 3β-methoxy-PREG) is a synthetic derivative of pregnenolone (3β-hydroxypregn-5α-en-20α-one), the natural precursor of steroid hormones, and in particular of neurosteroids. The 3β-methoxy function of 3β-methoxy-PREG prevents its conversion to its neuroactive metabolites. 3β-methoxy-PREG is believed to modulate the microtubule through its binding at microtubule-associated protein2 (MAP2) (Fontaine-Lenoir et al., 2006; Murakami et al., 2000). 3β-methoxy-PREG may therefore stimulate neuronal plasticity, as shown by its efficacy to enhance neurite extension of PC12 cells (Fontaine-Lenoir et al., 2006).

It has been shown that 3β-methoxy-PREG shows rapid and persistent antidepressant-like properties in stress-related animal models of depressive disorders:

U.S. Pat. No. 8,334,278 shows that 3β-methoxy-PREG:

decreases immobility of naïve adult male Sprague Dawley rats in the forced swimming test (FST), similarly to fluoxetine (an SSRI).

increases memory retention in naïve adult male Sprague Dawley rats in the Novel object recognition test (NOR), and induces recovery of memory deficit in the NOR test in social-isolated adult male Sprague Dawley rats. Social-isolated adult male Sprague Dawley rats were obtained by rearing them in isolation from the time of weaning and throughout adulthood. This social isolation protocol creates a stress that induces a series of hippocampal structural and molecular deficits paralleled by behavioural alterations resembling a stress-induced depressive-like state (Weiss and Feldon, Psychopharmacology 2001; Bianchi et al., EJN 2006).

Bianchi and Baulieu, 2012 presents the same data as U.S. Pat. No. 8,334,278 and additionally shows that 3β-methoxy-PREG:

decreased immobility of social-isolated adult male Sprague Dawley rats in the forced swimming test (FST), similarly to although more rapidly than fluoxetine (an SSRI), and recovered increased anxiety of social-isolated adult male Sprague Dawley rats in the subchronic phase (8 days of daily injections) but not in the acute phase (2 days of daily injections) in the Elevated plus maze (EPM) test, similarly to although more efficiently than fluoxetine.

Paresys et al., 2015 tested 3β-methoxy-PREG in tree shrews exposed to chronic psychosocial stress.

The tree shrew (Tupaia belangeri) is a day-active animal phylogenetically close to primates. Prolonged psychosocial stress was created in male tree shrews by a recurrent introduction of one male into the territory of another male to develop a dominant/subordinate relationship. The biobehavioral responses observed in subordinate tree shrews are similar to the symptoms observed in depressed patients. In this model, stress-induced alterations include social avoidance, cortisol and noradrenaline increase, elevation of core body temperature and sleep disturbances.

A 4-week daily administration of 3β-methoxy-PREG was found to abolish stress-triggered avoidance behavior and to prevent hormone hypersecretion, hypothermia and sleep disturbances, in a manner similar to fluoxetine (an SSRI).

Based on the above finding, 3β-methoxy-PREG has thus already been proposed for the treatment of depressive disorders.

However, as clearly appears above, animal models used in U.S. Pat. No. 8,334,278, in Bianchi and Baulieu, 2012 and in Paresys et al., 2015 are stress-related animal models of depressive disorders, in which depressive symptoms or behaviors are created by imposing acute or chronic stress to the animals.

As explained above, such stress-related animal models of depressive disorders are not suitable for predicting therapeutic efficiency on TRD, since TRD is associated to the presence of risk factors for depression, which predispose to the precipitation of depressive episodes by relatively low levels of stress. This is for instance illustrated by the fact that in all these data, the action of 3β-methoxy-PREG was similar to, although sometimes more rapid or more pronounced than fluoxetine, an SSRI antidepressant known to be inefficient in the treatment of TRD.

Data available for 3β-methoxy-PREG thus supported the use of this compound in the treatment of conventional depressive disorders, which may be treated by other antidepressant drugs such as SSRIs, but not of TRD, in which SSRIs are known to be generally inefficient.

SUMMARY OF THE INVENTION

However, in the context of the present invention, the inventors surprisingly found that 3β-methoxy-PREG is able to significantly and specifically reduce depressive symptoms in a rat model of treatment-resistant depression. More particularly, the inventors found that 3β-methoxy-PREG is able to significantly and rapidly reduce the anxiodepressive-like behavior observed in the Wistar Kyoto rat strain (WKY), a spontaneous model of depressive disorders (Pare and Redei, 1993). This strain was initially developed as a normotensive control strain for the spontaneously hypertensive rat strain, derived from the Wistar (WI) rats (Okamoto and Aoki, 1963). It was then found that WKY consistently demonstrate exaggerated behavioral and physiological responses to stress. In comparison to others strains, the WKY is one of the most susceptible to developing learned helplessness (Pare, 1994) and demonstrates higher levels of behavioral immobility at baseline in the forced swimming test (FST; (Armario et al., 1995)). Interestingly, the depressive-like state observed in WKY is known for its resistance to treatment by selective serotonin transporters inhibitors (SSRIs) such as fluoxetine (Griebel et al., 1999; Lopez-Rubalcava and Lucki, 2000), making this rat strain a model of treatment-resistant depression (TRD).

By comparison to data previously presented in U.S. Pat. No. 8,334,278, in Bianchi and Baulieu, 2012 and in Paresys et al., 2015, in which the action of 3β-methoxy-PREG was found to be similar to, although sometimes more rapid or more pronounced than fluoxetine, these new data show that, contrary to fluoxetine that is known to be inefficient for treatment of TRD in WKY rats, 3β-methoxy-PREG is able to significantly and rapidly reduce the anxiodepressive-like behavior observed in WKY rats, and may thus further be used in the treatment of TRD.

These new data also show superiority of the antidepressant effects of 3β-methoxy-PREG compared to ketamine in WKY rats, in two tests:

When assessing activity in open-arms of the elevated-plus maze test (EPM, showing anxiety-related behavior), acute administration of MAP4343 significantly increased the open-arm (OA) index by 165% (p<0.05) when compared to WKY receiving vehicle alone, whereas acute administration of ketamine did not induce significant change of the OA index as compared to WKY receiving vehicle alone (−29%, p=0.72) (see FIG. 5D).

In the forced swimming test (FST, showing depressive-like behavior), acute administration (4 days) of MAP4343 was found to induce a significant reduction in the time of immobility when compared to WKY rats receiving vehicle alone. While administration of ketamine also decreased the immobility time, the reduction was not significant when compared to WKY receiving vehicle, contrary to MAP4343 administration (see FIG. 6C).

The present invention thus relates to a compound of formula (I):

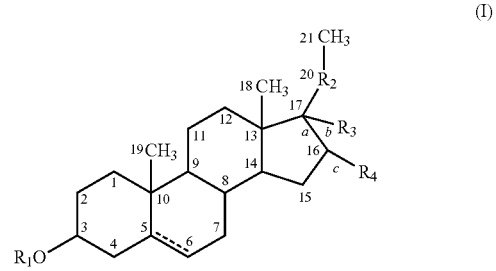

wherein:
------ independently represents a single or a double bond;
$R_1$ represents a $C_1$-$C_4$ alkyl;
$R_2$ represents —CO—; —CH(OH)— or —CH(O—COCH$_3$)—; and
$R_3$ represents H or CHCl$_2$ and $R_4$ represents H or CH$_3$, or $R_3$ and $R_4$ together represent

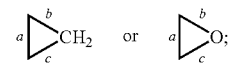

or a pharmaceutically acceptable salt thereof,
for use in the treatment of treatment-resistant depression.

The present invention also relates to a method for treating treatment-resistant depression in a subject in need thereof, comprising administering to said patient a therapeutically efficient amount of a compound of formula (I):

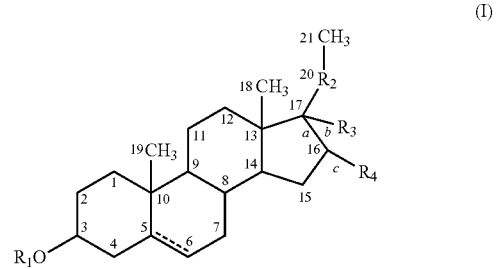

wherein:
------ independently represents a single or a double bond;
$R_1$ represents a $C_1$-$C_4$ alkyl;
$R_2$ represents —CO—; —CH(OH)— or —CH(O—COCH$_3$)—; and
$R_3$ represents H or CHCl$_2$ and $R_4$ represents H or CH$_3$, or $R_3$ and $R_4$ together represent

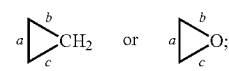

or a pharmaceutically acceptable salt thereof.

DESCRIPTION OF THE DRAWINGS

The patent or application file contains at least one drawing executed in color. Copies of this patent or patent application publication with color drawings will be provided by the United States Patent and Trademark Office upon request and payment of the necessary fee.

FIG. 1. Test of progesterone receptor agonist activity.

FIG. 4A: Locomotor activity of SD (white bar), WI (grey bar) and WKY rats (black bar) evaluated in the open-field arena by measuring the total distance travelled (cm) during 3 min. FIG. 4B-C: Anxious-like behavior of SD (white bar), WI (grey bar) and WKY rats (black bar) evaluated by measuring either the number of entries (FIG. 4B) or the time spent (in sec; FIG. 4C) in the central square of the open-field arena. FIG. 4D: Anxious-like behavior of SD (white bar), WI (grey bar) and WKY rats (black bar) evaluated in elevated-plus maze by measuring the open-arm index (time spent in the open arms (sec)/[time spent in open arms (sec)+time spent in closed arms (sec)]). E: Depressive-like behavior of SD (white bar), WI (grey bar) and WKY rats (black bar) evaluated in the forced-swimming test by measuring the immobility time (in seconds). Data are means±SEM from 11-14 independent rats per group. $p<0.01$ and *$p<0.001$ as compared to SD rats; #$p<0.05$ and ####$p<0.001$ as compared to indicated groups (One-way ANOVA followed by the Fisher LSD post-hoc test to compare mean of each group).

FIG. 5A: Locomotor activity (LMA) in WKY rats receiving vehicle or treated with MAP4343 (10 mg/kg), fluoxetine (10 mg/kg) or ketamine (30 mg/kg;). Data (means±SEM, n=11-19) are expressed as the total distance measured in the open-field arena during 3 min. FIG. 5B-C: Evaluation in open-field arena of anxious-like behavior of WKY rats receiving vehicle or treated with either MAP4343 (10 mg/kg), fluoxetine (10 mg/kg) or ketamine (30 mg/kg). Data (means±SEM, n=10-18 rats per group) are expressed as either the number of entries (FIG. 5B) or the time spent (FIG. 5C) in the central square of the arena. FIG. 5D: Evaluation in elevated-plus maze of anxious-like behavior of WKY rats receiving vehicle or treated with either MAP4343 (10 mg/kg), fluoxetine (10 mg/kg) or ketamine (30 mg/kg). Data (means±SEM, n=11-20 rats per group) are expressed as open-arm index. $p<0.01$ and *$p<0.001$ as compared to indicated groups (One-way ANOVA followed by the Fisher LSD post-hoc test).

FIG. 6A-B: Dose-response efficacy of MAP4343 in forced-swimming test. WI (FIG. 6A) and WKY (FIG. 6B) rats were treated with a dose ranging of MAP4343 (1, 5, 10 and 15 mg/kg respectively) or received only vehicle. Data (means±SEM, n=7-8 rats per group) are expressed as the immobility time in seconds. *$p<0.05$ as compared to the respective "vehicle" group in A and B (One-way ANOVA followed by the Fisher LSD post-hoc test). FIG. 6C: Comparison of the antidepressant-like efficacy of MAP4343 (10 mg/kg) with fluoxetine (10 mg/kg) and ketamine (30 mg/kg) in forced-swimming test. WKY rats received vehicle or were treated with MAP4343 (10 mg/kg), fluoxetine (10 mg/kg) or ketamine (30 mg/kg). Data (means±SEM, n=10-22 rats per group) are expressed as the immobility time in seconds. *$p<0.05$ and ***$p<0.001$ as compared to indicated groups (One-way ANOVA followed by the Fisher LSD post-hoc test).

FIG. 8A: Scheme representing the open-field arena within which two objects were introduced. During the first 5-min session, called "familiarization trial", the two objects were identical, while during the second 5-min session, called "choice session"; one object was replaced by a novel object, never explored by the rat.
FIG. 8B: Histograms showing the time spent to explore the novel object in WI and WKY rats after chronic administration with MAP4343, as compared to control rats receiving only vehicle.
FIG. 8C: Histograms showing the total exploratory time in Wistar and Wistar Kyoto rats after chronic administration with MAP4343, as compared to control rats receiving only vehicle. Data, expressed as seconds, are means±SEM from n=5-8 independent animals per group.
**$p<0.01$ and $p<0.05$ as compared to indicated groups.

FIG. 9A: Representative confocal images in showing, in dentate gyrus of hippocampus, the BrdU-positive cells (upper images, in green), the Neu-N-positive-neurons (central images, in red), and the merge of co-labelled cells (lower images) in WKY rats receiving only vehicle. FIG. 9B: Representative confocal images in showing, in dentate gyrus of hippocampus, the BrdU-positive cells (upper images, in green), the Neu-N-positive-neurons (central images, in red), and the merge of co-labelled cells (lower images) in WKY rats treated with MAP4343. FIG. 9C: Histograms showing the total number of newly-formed neurons (co-labelled with BrdU and Neu-N) in dentate gyrus of hippocampus from WKY rats either treated with MAP4343 (grey bar) or receiving only vehicle (black bar). Data are means±SEM from n=5 independent animals per group. **$p<0.01$ as compared to rats receiving vehicle.

DETAILED DESCRIPTION OF THE INVENTION

Definitions

Figure 1:
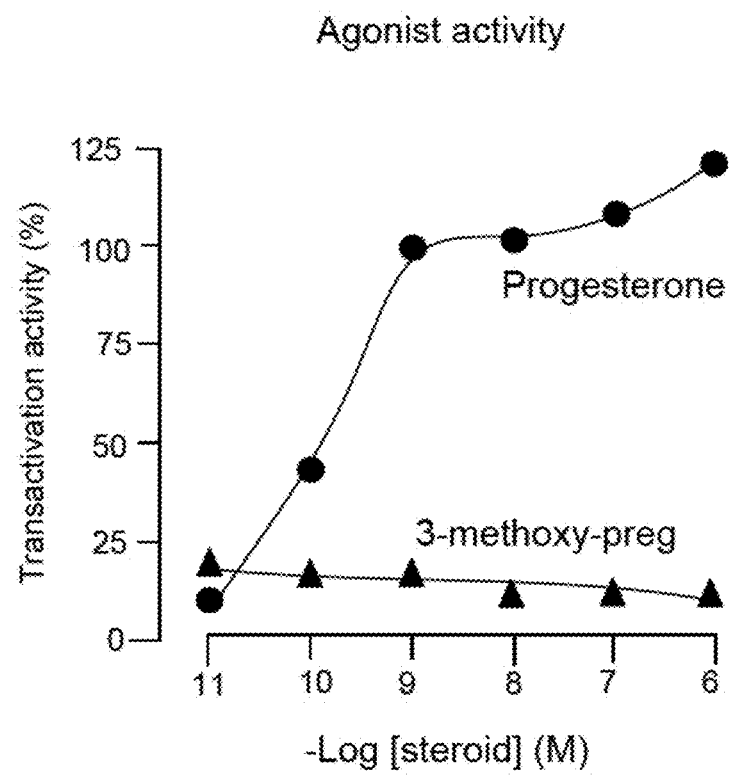

"Treatment-resistant depression" or "TRD" is defined as a major depressive disorder (as defined in Diagnostic and Statistical Manual of Mental Disorders, Fifth Edition, generally referred to as DSM-V or DSM-5) that does not respond to at least one antidepressant treatment or that does not evolve favorably under the influence of this or these treatments. The concept of resistant depression thus necessarily implies the concept of previous, failed, drug treatment(s).

TRD may be evaluated based on Thase & Rush classification (Thase & Rush, 1997), which defines 5 stages of TRD:

Stage 1: resistance to 1 adequate treatment,
Stage 2: failure of two adequate treatments from two different pharmacological classes,
Stage 3: resistance to two different classes and to one tricyclic,
Stage 4: resistance to two different classes and to tricyclics and to MAOIs,
Stage 5: as stage 4, plus resistant to ECT.

By "adequate treatment", it is meant an antidepressant drug therapy administered at a sufficient dosage and for a sufficient time (at least 4 weeks and usually 6 weeks).

Conventional antidepressant drugs include:

Selective serotonin reuptake inhibitors (SSRIs), which are often used as a first medicament in the treatment of depression.

SSRIs include fluoxetine (Prozac, Selfemra), paroxetine (Paxil, Pexeva), sertraline (Zoloft), citalopram (Celexa) and escitalopram (Lexapro).

Serotonin and norepinephrine reuptake inhibitors (SNRIs).

SNRIs include duloxetine (Cymbalta), venlafaxine (Effexor XR), desvenlafaxine (Pristiq, Khedezla) and levomilnacipran (Fetzima).

Norepinephrine and dopamine reuptake inhibitors (NDRIs), such as Bupropion (Wellbutrin, Aplenzin, Forfivo XL).

Tricyclic antidepressants, which are often used when an SSRI treatment has failed, because they tend to cause more side effects.

Tricyclic antidepressants include imipramine (Tofranil), nortriptyline (Pamelor), amitriptyline, doxepin, trimipramine (Surmontil), desipramine (Norpramin) and protriptyline (Vivactil).

Monoamine oxidase inhibitors (MAOIs), which are often used when other medications have failed, because they can have serious side effects. MAOIs include tranylcypromine (Parnate), phenelzine (Nardil) and isocarboxazid (Marplan).

Atypical antidepressants, that don't fit neatly into any of the other antidepressant categories.

These include trazodone (Oleptro), mirtazapine (Remeron), vortioxetine (Brintellix), and vilazodone (Viibryd).

By "response" or "efficient treatment" or "therapeutic benefit" is meant a reduction of scores on depression scales (Hamilton Depression Rating Scale-17 or Montgomery-Åsberg Depression Rating Scale) greater than 50%, maintained for at least 3 months.

The Hamilton Depression Rating Scale (also referred to as "HDRS" or "HAM-D") is a multiple item questionnaire used to provide an indication of depression, and as a guide to evaluate recovery. The questionnaire is designed for adults and is used to rate the severity of their depression by probing mood, feelings of guilt, suicide ideation, insomnia, agitation or retardation, anxiety, weight loss, and somatic symptoms. The original 1960 version contains 17 items to be rated (HRSD-17), but three other questions (18-20) are used to provide additional clinical information although they are not added to the total score. Each item on the questionnaire is scored on a 3, 4 or 5 point scale (from 0 to 2 points, from 0 to 3 points, or from 0 to 4 points), depending on the item, and the total score may vary between 0 and 53. For HRSD-17, a score of 0-7 is considered to be normal. Scores of 20 or higher indicate moderate, severe, or very severe depression, and are usually required for entry into a clinical trial. Questions 18-20 may be recorded to give further information about the depression (such as whether diurnal variation or paranoid symptoms are present), but are not part of the scale. A structured interview guide for the questionnaire is publicly available. Although Hamilton's original scale had 17 items, other versions were developed to include up to 29 items (HRSD-29).

The Montgomery-Åsberg Depression Rating Scale (also referred to as "MADRS") is a ten-item diagnostic questionnaire which psychiatrists use to measure the severity of depressive episodes in patients with mood disorders. It was designed in 1979 by British and Swedish researchers as an adjunct to the HDRS which would be more sensitive to the changes brought on by antidepressants and other forms of treatment than the HDRS was. There is, however, a high degree of statistical correlation between scores on the two measures. Each of the ten items yields a score of 0 to 6. The overall score ranges from 0 to 60. The questionnaire includes questions on the following symptoms 1. Apparent sadness 2. Reported sadness 3. Inner tension 4. Reduced sleep 5. Reduced appetite 6. Concentration difficulties 7. Lassitude 8. Inability to feel 9. Pessimistic thoughts 10. Suicidal thoughts. Usual cutoff points are:

0 to 6: normal/symptom absent
7 to 19: mild depression
20 to 34: moderate depression
>34: severe depression.

As explained above, in the context of the present invention, "response" or "efficient treatment" or "therapeutic benefit" is meant a reduction of HDRS-17 or MADRS score greater than 50%, maintained at least 3 months after an adequate treatment (as defined above).

A "therapeutically effective amount" corresponds to an amount necessary to impart therapeutic benefit to a subject, as defined above.

Conversely, by "resistance" to a particular treatment is meant either a reduction in scores on HDRS or MADRS depression scales of at most 50%, or a complete response (>50% reduction of HDRS or MADRS score) but maintained during less than 3 months after an adequate treatment (as defined above).

For the purpose of the present invention, the term "$C_1$-$C_4$ alkyl" is intended to mean any linear or branched saturated hydrocarbon radical having from one to four carbon atoms. Examples of $C_1$-$C_4$ alkyl groups include a methyl ($CH_3$) or an ethyl ($C_2H_6$) group.

"Pharmaceutically acceptable salts" refer to salts that are suitable for use in contact with the tissues of humans and animals without undue toxicity, irritation, allergic response, and the like. Examples of suitable salts include salts of alkali metals such as potassium, sodium, lithium, salts of alkaline earth metals such as calcium, magnesium and acid addition salts with inorganic and organic acids are, but are not limited to, hydrochloric acid, nitric acid, sulphuric acid, phosphoric acid, sulphuric acid, citric acid, formic acid, fumaric acid, maleic acid, lactic acid, malic acid, acetic acid, succinic acid, hemisuccinic acid, tartaric acid, methane-sulfonic acid, p-toluenesulphonic acid, trifluoro acetic acid and the like.

Compounds for Use in the Treatment of TRD

The present invention relates to a compound of formula (I):

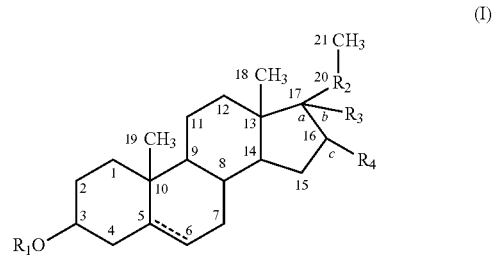

wherein:
------ independently represents a single or a double bond;
$R_1$ represents a $C_1$-$C_4$ alkyl;

$R_2$ represents —CO—; —CH(OH)— or —CH(O—COCH$_3$)—; and $R_3$ represents H or CHCl$_2$ and $R_4$ represents H or CH$_3$, or $R_3$ and $R_4$ together represent

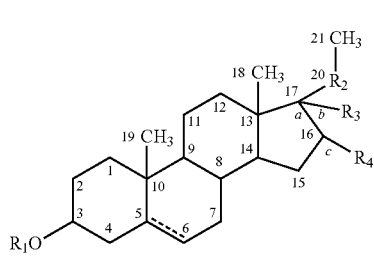

or a pharmaceutically acceptable salt thereof, for use in the treatment of treatment-resistant depression (TRD).

The present invention also relates to a method for treating treatment-resistant depression (TRD) in a subject in need thereof, comprising administering to said patient a therapeutically efficient amount of a compound of formula (I):

(I)

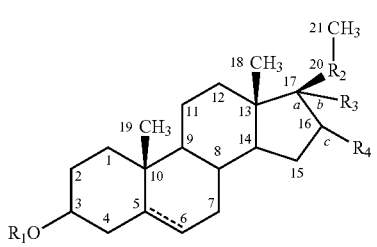

wherein:

------ independently represents a single or a double bond;

$R_1$ represents a C$_1$-C$_4$ alkyl;

$R_2$ represents —CO—; —CH(OH)— or —CH(O—COCH$_3$)—; and $R_3$ represents H or CHCl$_2$ and $R_4$ represents H or CH$_3$, or $R_3$ and $R_4$ together represent

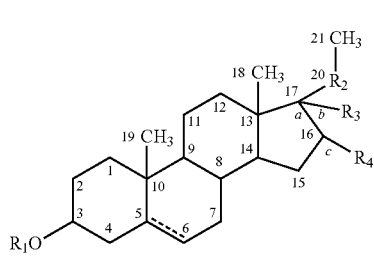

or a pharmaceutically acceptable salt thereof.

Stereochemistry may be important for activity of the compound of formula (I). As a result, in the above therapeutic uses, the compound is preferably of a compound of formula (Ib), and even more preferably a compound of formula (Ic):

(Ib)

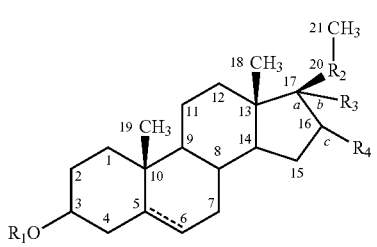

-continued (Ic)

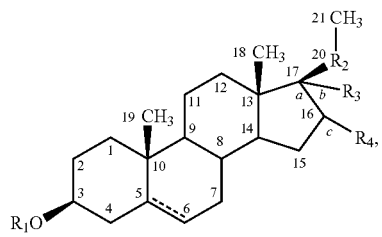

wherein:

------ independently represents a single or a double bond;

$R_1$ represents a C$_1$-C$_4$ alkyl;

$R_2$ represents —CO—; —CH(OH)— or —CH(O—COCH$_3$)—; and $R_3$ represents H or CHCl$_2$ and $R_4$ represents H or CH$_3$, or $R_3$ and $R_4$ together represent

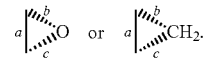

Preferably, in the above therapeutic uses, the compound is of formula (II):

(II)

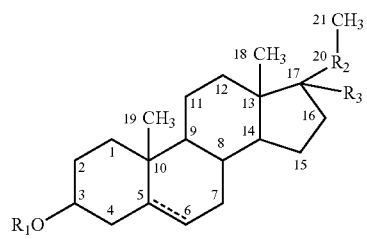

wherein:

------ represents a single or a double bond;

$R_1$ represents a C$_1$-C$_4$ alkyl;

$R_2$ represents —CO— or —CH(OH)—; and $R_3$ represents H or CHCl$_2$.

In formula (II) also, stereochemistry may be important for activity of the compound. As a result, in the above therapeutic uses, the compound is preferably of a compound of formula (IIb), and even more preferably a compound of formula (IIc):

(IIb)

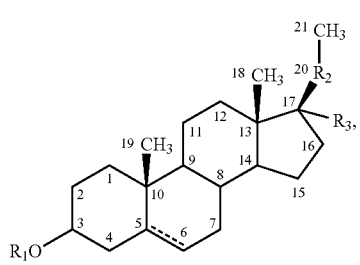

-continued

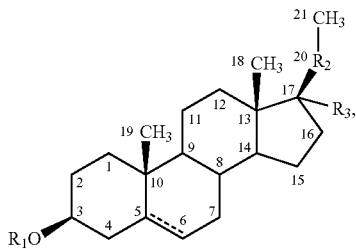

(IIc)

wherein ------, $R_1$, $R_2$, and $R_3$ are as defined above for formula (II).

In a preferred embodiment of anyone of formulas (I), (Ib), (Ic), (II), (IIb), and (IIc) above, $R_1$ is $CH_3$.

Alternatively or in combination, in anyone of formulas (I), (Ib), (Ic), (II), (IIb), and (IIc) above, ------ is preferably a double bond. In addition, in anyone of formulas (I), (Ib), (Ic), (II), (IIb), and (IIc) above, when ------ represents a simple bond, the hydrogen atom attached to the carbon atom in position 5 is preferably in α.

Alternatively or in combination, in anyone of formulas (I), (Ib), (Ic), (II), (IIb), and (IIc) above, $R_2$ is preferably —CO—.

Alternatively or in combination, in anyone of formulas (I), (Ib), (Ic), (II), (IIb), and (IIc) above, $R_3$ represents H.

It should be noted that any preferred bond/group for any of the substituents may be combined with any other preferred bond/group for another of the substituents.

Preferred compounds for the above therapeutic uses are those described in Table 1 below, or any pharmaceutically acceptable salt thereof:

TABLE 1

| Preferred compounds for use in the invention | |
|---|---|
| Compound | Formula |
| 3-methoxy-pregna-5-ene-20-one | (structure) |
| 3-methoxy-pregna-5-ene-20-ol | (structure) |
| 3-methoxy-pregna-5-ene-20-one-17-dichloromethyl | (structure) |
| 3-methoxy-5-pregnane-20-one | (structure) |
| 3-methoxy-5-pregnane-20-ol | (structure) |

A particularly preferred compound is 3-methoxy-pregna-5-ene-20-one, of formula:

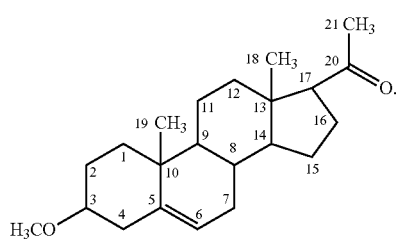 [SMILES: COC1CCC2(C)C(=CCC3C2CCC2(C)C(C(C)=O)CCC32)C1]

For compounds also, stereochemistry may be important for activity of the compound. As a result, in the above therapeutic uses, the compound is preferably selected from those described in Table 2 below, or any pharmaceutically acceptable salt thereof:

TABLE 2

Preferred compounds for use in the invention

| Compound | Formula |
|---|---|
| 3β-methoxy-pregna-5-ene-20-one | |
| 3β-methoxy-pregna-5-ene-20β-ol | |
| 3β-methoxy-pregna-5-ene-20α-ol | |
| 3β-methoxy-pregna-5-ene-20-one-17α-dichloromethyl | |
| 3β-methoxy-5α-pregnane-20-one | |
| 3β-methoxy-5α-pregnane-20β-ol | |
| 3β-methoxy-5α-pregnane-20α-ol | |

A particularly preferred compound is 3β-methoxy-pregna-5α-ene-20α-one (3β-methoxy-PREG), of formula:

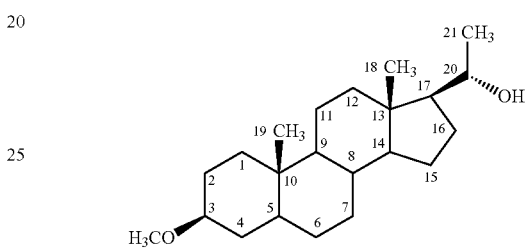

Preparation of the Compounds

The above defined compounds or pharmaceutically acceptable salts thereof may be prepared easily using conventional synthesis chemistry, starting from corresponding commercially available compounds with an OH group in position C3.

In particular, 3β-methoxy-PREG may be prepared from pregnenolone by addition of p-toluenesulfonyl chloride in pyridine, stirring of the mixture, addition of distilled water, cooling of the reaction to 0° C., filtration and drying under vacuum to yield pregnenolone tosylate. Pregnenolone tosylate is then refluxed with methanol for 4 hours. After cooling and evaporation of the solvent, the crude reaction product is washed in 10% sodium bicarbonate solution. After drying the organic phase over $Na_2SO_4$, it is evaporated dry under reduced pressure to yield 3β-methoxy-PREG. A precise protocol is disclosed in Example 1 of WO2004067010A1. 3β-methoxy-PREG is also commercially available, for instance from Steraloids Inc (Newport, R.I., USA). Similar methods may be used for preparation of other non-bioconvertible $C_3$-substituted pregnenolone derivatives useful in the context of the present invention, starting from corresponding commercially available compounds with an OH group in position C3.

Administration of the Compounds

The above defined compounds or pharmaceutically acceptable salts thereof, and in particular 3β-methoxy-PREG or pharmaceutically acceptable salts thereof, may be administered to any subject suffering from treatment-resistant depression, in particular to any human subject suffering from treatment-resistant depression.

The above defined compounds or pharmaceutically acceptable salts thereof, and in particular 3β-methoxy-PREG or pharmaceutically acceptable salts thereof, may be administered to a (preferably human) subject suffering from treatment-resistant depression via any suitable administration route, including oral, intravenous, transdermal, subcutaneous, intranasal, topical, sublingual, and rectal routes. Preferred administrations routes include oral, subcutaneous, and intranasal routes.

Depending on the selected route of administration, those skilled in the art will know how to formulate the above defined compounds or pharmaceutically acceptable salts thereof in order to optimize in vivo delivery and bioavailability. In particular, the above defined compounds or pharmaceutically acceptable salts thereof, and in particular 3β-methoxy-PREG or pharmaceutically acceptable salts thereof, may be formulated with suitable pharmaceutically acceptable carriers, excipients, vehicles, preservatives, solubilizing agents, stabilizers, wetting agents, emulsifiers, sweeteners, dyes, flavoring, salts intended to modify osmotic pressure, buffers, taste correctors, and antioxidants. These compounds are well-known to those skilled in the art. Details on these chemicals can be found in the latest edition of Remington's Pharmaceutical Sciences (Maack Publishing Co., Easton, Pa.). The selection of the optimal delivery formulation will be selected by those skilled in the art depending on the selected administration route.

Suitable unit dose administration formulations for oral administration notably include tablets, coated tablets, pills, capsules and soft gelatin capsules, oral powders, granules, solutions and suspensions.

When a solid composition in tablet form is prepared, the principal active ingredient may be mixed with a pharmaceutical vehicle, such as gelatin, starch, lactose, stearic acid or magnesium stearate, talc, gum arabic or analogues. The tablets may be coated with saccharose or other suitable materials or even be treated so as to have a prolonged or delayed activity and to release continuously a predetermined quantity of the active ingredient.

A capsule preparation may be obtained by mixing the active ingredient with a thinner and pouring the mixture obtained into soft or hard capsules, with excipients such as vegetable oils, waxes, fats, semi-solid or liquid polyols, etc.

A preparation in syrup or elixir form can contain the active ingredient together with a sweetener, an antiseptic, as well as an agent giving taste and a suitable dye. Excipients may be used, such as water, polyols, saccharose, invert sugar, glucose, etc.

Powders or water-dispersible granules may contain the active ingredient in a mixture with dispersing agents, wetting agents, and suspending agents, together with taste correctors and sweeteners.

For intravenous or intranasal administration, aqueous suspensions, isotonic saline solutions, or sterile, injectable solutions that contain pharmacologically compatible dispersing agents and/or wetting agents may be used. As an excipient, water, alcohols, polyols, glycerol, vegetable oils, etc., may be used.

For subcutaneous administration, any suitable pharmaceutically acceptable vehicle may be used. In particular, a pharmaceutically acceptable oil vehicle, such as sesame oil, may be used.

For topical administration, compositions may be presented in the form of a gel, a paste, an ointment, a cream, a lotion, an aqueous or aqueous-alcohol liquid suspension, an oily solution, a dispersion of the lotion or serum type, an anhydrous or lipophilic gel, an emulsion with a liquid or semi-solid milk-type consistency obtained by dispersing a fatty phase in an aqueous phase or vice versa, suspensions or emulsions of a soft or semi-solid cream- or gel-type consistency, or alternatively microemulsions, microcapsules, microparticles, or vesicular dispersions of the ionic and/or nonionic type. These compositions are prepared according to standard methods. Moreover, a surfactant can be included in the composition in order to enable deeper penetration of the above defined compounds or pharmaceutically acceptable salts thereof, and in particular 3β-methoxy-PREG or pharmaceutically acceptable salts thereof. An agent enabling an increased penetration may be selected, for example, from mineral oil, ethanol, triacetin, glycerin and propylene glycol; cohesion agents are selected, for example, from the group comprising polyisobutylene, polyvinyl acetate, polyvinyl alcohol, and thickening agents.

For rectal administration, suppositories, which are prepared with binders that melt at rectal temperatures, for example cocoa butter or semi-solid or liquid polyols such as polyethylene glycols, waxes, natural or hydrogenated oils, fats, etc., can be used.

The above defined compounds or pharmaceutically acceptable salts thereof, and in particular 3β-methoxy-PREG or pharmaceutically acceptable salts thereof, may be administered to a (preferably human) subject suffering from treatment-resistant depression at any dose suitable for obtaining a therapeutic effect. In particular, a suitable dose for humans may be in the range of 50 to 2000 mg/day, in particular in the range of 50 to 1750 mg/day, in the range of 50 to 1500 mg/day, in the range of 50 to 1250 mg/day, in the range of 50 to 1000 mg/day, in the range of 50 to 750 mg/day, in the range of 50 to 500 mg/day, in the range of 100 to 2000 mg/day, in particular in the range of 100 to 1750 mg/day, in the range of 100 to 1500 mg/day, in the range of 100 to 1250 mg/day, in the range of 100 to 1000 mg/day, in the range of 100 to 750 mg/day, in the range of 100 to 500 mg/day, in the range of 250 to 2000 mg/day, in particular in the range of 250 to 1750 mg/day, in the range of 250 to 1500 mg/day, in the range of 250 to 1250 mg/day, in the range of 250 to 1000 mg/day, in the range of 250 to 750 mg/day, in the range of 250 to 500 mg/day, in the range of 500 to 2000 mg/day, in the range of 500 to 1750 mg/day, in the range of 500 to 1500 mg/day, in the range of 500 to 1250 mg/day, in the range of 500 to 1000 mg/day, or in the range of 500 to 750 mg/day.

The administered dose may vary depending on the subject age, body surface area or body weight, or on the administration route and associated bioavailability. Such dose adaptation is well known to those skilled in the art.

TRD Patients to be Treated

The above defined compounds or pharmaceutically acceptable salts thereof, and in particular 3β-methoxy-PREG or pharmaceutically acceptable salts thereof, may be used for treating any patient afflicted with TRD, and in particular any stage of TRD as defined by Thase & Rush classification, including stage 1, stage 2, stage 3, stage 4 or stage 5.

The following examples merely intend to illustrate the present invention.

EXAMPLES

Example 1. Activity of 3β-Methoxy-Pregnenolone on Progesterone Receptor

The capacity of 3β-methoxy-pregnenolone to display progesterone activity, and thus to be considered as a progestin, was tested by assaying the activity of 3-methoxy-pregnenolone on progesterone receptor.

Indeed, progesterone is an agonist of progesterone receptor, as are all progestins. In contrast, compounds able to inhibit progesterone activity on its receptor are called progesterone receptor antagonists.

Methods

The main experimental setting used is the following: HEK293T cells were transiently transfected, using calcium phosphate precipitation technology, with expression vectors pSG5hPR (which permits expression of human progesterone receptor (PR)), pFC31-luc (contains the luciferase gene under the control of the MMTV promoter, which is in turn activated by binding of a progestin to progesterone receptor) and pcbetagal (which permits expression of betagalactosidase), and cultured during 24 hours with increasing amounts of various compositions:

Test of Progesterone Receptor Agonist Activity: Transfected Cells were Cultured with Increasing Amounts of Progesterone or 3-Methoxy-Pregnenolone With this setting, a compound with progesterone receptor agonist activity permits a transactivation activity resulting in the expression of luciferase (since the binding of a progestin to PR results in activation of the MMTV promoter, which directs the expression of luciferase).

In contrast, a compound without progesterone receptor agonist activity does not permit a transactivation activity and luciferase is not expressed (since PR is not activated and thus does not activate the MMTV promoter);

Test of progesterone receptor agonist activity: transfected cells were cultured with progesterone (1 nM) and increasing amounts of RU486 (a well-known progesterone receptor antagonist) or 3-methoxy-pregnenolone.

With this setting, a compound with progesterone receptor antagonist activity competes with progesterone for the occupation of progesterone receptor and results in a progressive loss of transactivation activity when the amount of this compound is increased compared to progesterone.

Results

The results obtained with experimental setting 1 (test of progesterone receptor agonist activity) are displayed in FIG. 1.

FIG. 1 clearly shows that, contrary to progesterone, which permits a transactivation activity leading to the expression of luciferase, 3-methoxy-pregnenolone does not permit such a transactivation activity, even at the highest tested concentrations, thus demonstrating that 3β-methoxy-pregnenolone does not have progesterone receptor agonist activity, and cannot thus be considered as a progestin.

Figure 2:
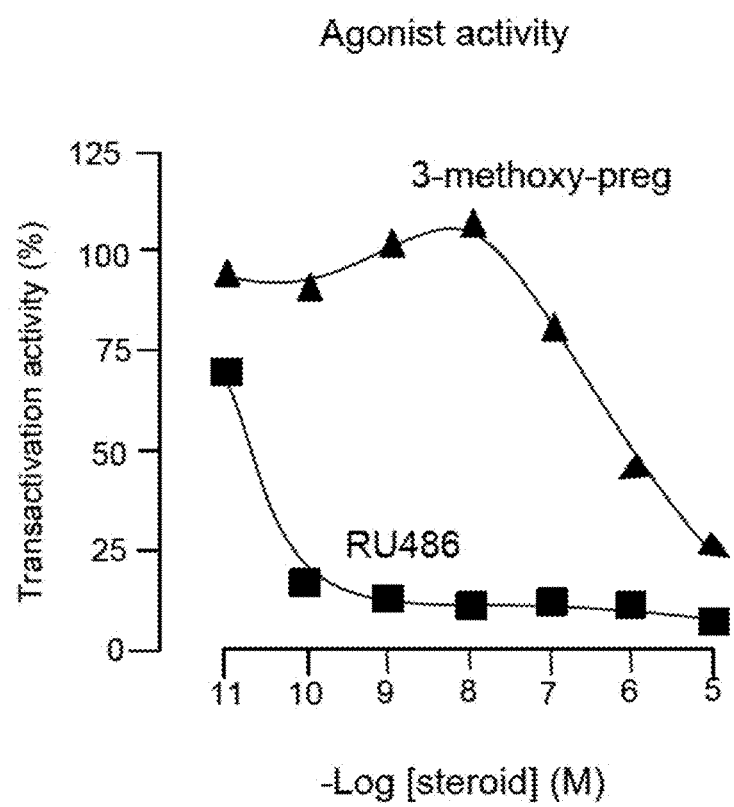
FIG. 2. Test of progesterone receptor antagonist activity.

The results obtained with experimental setting 2 (test of progesterone receptor antagonist activity) are displayed in FIG. 2.

These results unambiguously show that even if 3β-methoxy-pregnenolone does not have the very high antagonist activity of RU486, it is a weak progesterone receptor antagonist.

Example 2. 3β-methoxy-PREG has No Androgenic, Estrogenic, Glucocorticoid and Mineral Corticoid Activity Binding affinity of 3β-methoxy-PREG (MAP4343) for receptors of steroid hormones was evaluated using radioligand binding assays.

MAP4343 (10 μM) was ineffective (<25% inhibition) in displacing specific radioligands from the following binding sites: Mineralocorticoid Receptor (MR), Androgen Receptor (AR), Estrogen Receptors (ERα and ERβ) and Glucocorticoid Receptor (GR). The results are summarized below in Table 3 below.

TABLE 3

Affinity of MAP4343 (10 μM) for steroid hormones receptors measured by radioligand binding assays. Biochemical assay results are presented as the percent inhibition of specific binding (significant responses: ≥50% inhibition). None of the results met significance criteria at concentrations used.

| Target | Ligand | Source | % inhibition* |
|---|---|---|---|
| MR | 4.5 nM [$^3$H] D-Aldosterone | Wistar Rat kidney | 25 |
| AR | 1.5 nM [$^3$H] Mibolerone | Rat recombinant E. coli | 18 |
| ER☐ | 0.5 nM [$^3$H] Estradiol | Human recombinant Sf9 cells | −8 |
| ER☐ | 0.5 nM [$^3$H] Estradiol | Human recombinant Sf9 cells | 16 |
| GR | 3 nM [$^3$H] Dexamethasone | Human HeLa S3 cells | 21 |

*Negative values correspond to stimulation of binding or enzyme activity

Example 3. 3β-Methoxy-PREG has No Significant Affinity for Receptors of the Central Nervous System MAP4343 has been screened for in vitro affinity to 80 different CNS neurotransmitters receptors using various validated binding assays.

The results show that MAP4343 has no significant affinity for any tested receptor including the ones traditionally associated with side effects or abuse liability. Results are summarized in following Table 4.

TABLE 4

In vitro affinity of MAP4343 (10 μM) for CNS neurotransmitter receptors associated with side effects and/or abuse liability. Data are the average of two individual assays for each receptor and are expressed as % inhibition of the control specific binding of the reference compound. Results showing an inhibition higher than 50% are considered to represent significant effects of the test compound. MAP4343 showed no significant effects on any of the tested receptor at the concentration used.

| Receptor family | Target | Ligand | Source | % Inhibition of control specific binding |
|---|---|---|---|---|
| Muscarinic (Cholinergic) | $M_1$ | [$^3$H] pirenzepine | Human recombinant (CHO cells) | −3 |
| | $M_2$ | [$^3$H] AF-DX 384 | Human recombinant (CHO cells) | 20 |
| | $M_3$ | [$^3$H] 4-DAMP | Human recombinant (CHO cells) | 3 |

TABLE 4-continued

In vitro affinity of MAP4343 (10 μM) for CNS neurotransmitter receptors associated with side effects and/or abuse liability. Data are the average of two individual assays for each receptor and are expressed as % inhibition of the control specific binding of the reference compound. Results showing an inhibition higher than 50% are considered to represent significant effects of the test compound. MAP4343 showed no significant effects on any of the tested receptor at the concentration used.

| Receptor family | Target | Ligand | Source | % Inhibition of control specific binding |
|---|---|---|---|---|
| | $M_4$ | [$^3$H] 4-DAMP | Human recombinant (CHO cells) | 20 |
| | $M_5$ | [$^3$H] 4-DAMP | Human recombinant (CHO cells) | 12 |
| Histaminergic | $H_1$ | [$^3$H] pyrilamine | Human recombinant (HEK-293 cells) | 9 |
| | $H_2$ | [$^{125}$I] APT | Human recombinant (CHO cells) | −21 |
| Noradrenergic | $\alpha_1$ | [$^3$H] prazosin | rat cerebral cortex | 4 |
| | $\alpha_2$ | [$^3$H] RX 821002 | rat cerebral cortex | 7 |
| | $\beta_1$ | [$^3$H] (−) CGP 12177 | Human recombinant (HEK-293 cells) | 1 |
| | $\beta_2$ | [$^3$H] (−) CGP 12178 | Human recombinant (CHO cells) | −4 |
| | Transporter | [$^3$H] nisoxetine | Human recombinant (CHO cells) | 3 |
| Serotoninergic | 5-HT$_{1A}$ | [$^3$H] 8-OH-DPAT | Human recombinant (HEK-293 cells) | 2 |
| | 5-HT$_{1B}$ | [$^{125}$I] CYP + (−) propranolol | rat cerebral cortex | 4 |
| | 5-HT$_{2A}$ | [$^3$H] ketanserin | Human recombinant (HEK-293 cells) | 1 |
| | 5-HT$_{2B}$ | [$^{125}$I] (±) DOI | Human recombinant (CHO cells) | −4 |
| | 5-HT$_{2C}$ | [$^3$H] mesulergine | Human recombinant (CHO cells) | 7 |
| | 5-HT$_3$ | [$^3$H] BRL 43694 | Human recombinant (CHO cells) | 10 |
| | 5-HT$_{5A}$ | [$^3$H] LSD | Human recombinant (CHO cells) | −5 |
| | 5-HT$_6$ | [$^3$H] LSD | Human recombinant (CHO cells) | 12 |
| | 5-HT$_7$ | [$^3$H] LSD | Human recombinant (CHO cells) | −11 |
| | Transporter | [$^3$H] imipramine | Human recombinant (CHO cells) | 3 |
| Dopaminergic | $D_1$ | [$^3$H] SCH 23390 | Human recombinant (CHO cells) | 2 |
| | $D_{2S}$ | [$^3$H] spiperone | Human recombinant (HEK-293 cells) | 6 |
| | $D_3$ | [$^3$H] spiperone | Human recombinant (CHO cells) | 8 |
| | $D_{4.4}$ | [$^3$H] spiperone | Human recombinant (CHO cells) | 6 |

TABLE 4-continued

In vitro affinity of MAP4343 (10 μM) for CNS neurotransmitter receptors associated with side effects and/or abuse liability. Data are the average of two individual assays for each receptor and are expressed as % inhibition of the control specific binding of the reference compound. Results showing an inhibition higher than 50% are considered to represent significant effects of the test compound. MAP4343 showed no significant effects on any of the tested receptor at the concentration used.

| Receptor family | Target | Ligand | Source | % Inhibition of control specific binding |
|---|---|---|---|---|
| | $D_5$ | [$^3$H] SCH 23390 | Human recombinant (GH4 cells) | −7 |
| | Transporter | [$^3$H] BTCP | Human recombinant (CHO cells) | |
| GABA | (non-selective) | [$^3$H] GABA | rat cerebral cortex | 2 |
| NMDA | PCP site | [$^3$H] TCP | rat cerebral cortex | −10 |
| Cannabinoid | $CB_1$ | [$^3$H] CP 55940 | Human recombinant (CHO cells) | 12 |
| Oppioid | $\delta_2$ | [$^3$H] DADLE | Human recombinant (CHO cells) | −3 |
| | κ | [$^3$H] U 69593 | rat recombinant (CHO cells) | 19 |
| | μ | [$^3$H] DAMGO | Human recombinant (HEK-293 cells) | 0 |

Example 4: Efficiency of 3β-methoxy-PREG in a Rat Model of Treatment-Resistant Depression In order to test efficiency of 3β-methoxy-PREG in the treatment of TRD, this compound was tested and compared to fluoxetine (an SSRI) and ketamine in a spontaneous rat model of TRD due to its resistance to SSRIs: the Wistar Kyoto rat strain (WKY). This strain was initially developed as a normotensive control strain for the spontaneously hypertensive rat strain, derived from the Wistar (WI) rats (Okamoto and Aoki, 1963). It was then found that WKY consistently demonstrate exaggerated behavioral and physiological responses to stress. In comparison to others strains, the WKY is one of the most susceptible to developing learned helplessness (Pare, 1994) and demonstrates higher levels of behavioral immobility at baseline in the forced swimming test (FST; (Armario et al., 1995)). Interestingly, the depressive-like state observed in WKY is known for its resistance to treatment by selective serotonin transporters inhibitors (SSRIs) such as fluoxetine (Griebel et al., 1999; Lopez-Rubalcava and Lucki, 2000), making this rat strain a model of treatment-resistant depression (TRD).

Materials and Methods

Animals

Height-week old male Sprague Dawley (SD), Wistar (WI) and Wistar Kyoto (WKY) rats were provided by Harlan Laboratories. Both untreated and treated rats were randomly housed grouped (3-4 per cage) during the whole period of experiments, in opaque plastic cages lined with sawdust and fitted with metal grid lids, in the same room under controlled conditions (21±1° C., 12 h/12 h light/dark cycles, lights on at 8 a.m., with food and water available ad libitum). The experiments were in accordance with the European Communities Council Directive (86/609/EEC) and approved by the internal committee for animal experimentation of MAPREG.

Preparation of Drugs

3β-methoxy-PREG (also referred to as "MAP4343" in Example 4) was dissolved in sesame oil by sonication using a Sonifer-450 (Branson Ultrasonics Corporation, Danbury, USA) during 1 cycle of 5 pulses in sesame oil. Fluoxetine (Biotrend, Köln, Germany) and Ketamine (Sigma-Aldrich, St-Quentin Fallvier, France) were dissolved in sterile saline solution (NaCl 0.9%). The drug formulations were prepared freshly each day of treatment. MAP4343 was administered subcutaneously (ranging of 1-15 mg/Kg/day) while fluoxetine and ketamine were injected intraperitonealy (10 mg/Kg/day and 30 mg/Kg/day, respectively).

Experimental Designs

Behavioral Characterization of WKY Rat Strain

Figure 3:
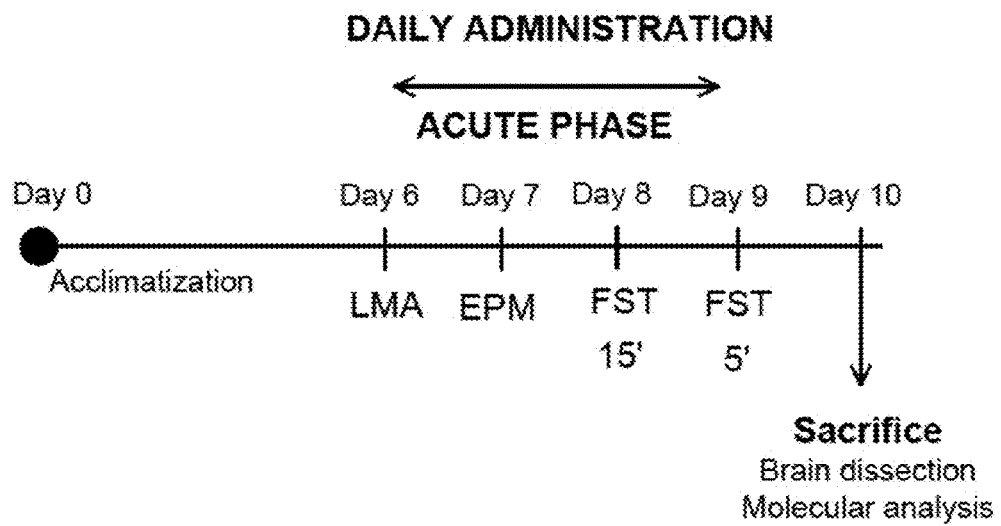
FIG. 3. Experimental design of the study. Scheme depicting the timing of treatments and behavioral experiments.

After a 6-day period of acclimatization, behavioral tests were performed on naïve untreated SD, WI and WKY rats, as depicted in FIG. 3. Animals were sacrificed 24 hours after the last behavioral test to perform analysis of α-tubulin isoforms and MAP2 phosphorylation.

Acute Treatments (4 Days)

After a 6-day period of acclimatization, all experimental groups received daily successive subcutaneous (250 μl per rat) and intraperitoneal (1 ml/kg) injections. WI rats received injection of vehicle (sesame oil+saline) while WKY rats were randomly assigned to three experimental groups, as follow: KWY rats receiving only vehicle (sesame oil+saline) and WKY rats treated with MAP4343 (10 mg/kg, s.c.; rats received in parallel i.p. injections of saline), fluoxetine (10 mg/kg i.p., rats received in parallel s.c. injections of sesame oil) or ketamine (30 mg/kg, i.p.; rats received in parallel s.c. injections of sesame oil) (see FIG. 3).

After, a 6-day period of acclimatization, the acute phase of treatment started for 4 days during behavioral tests were performed (FIG. 3). All animals were injected 1 h 30 before the starting of behavioral test.

Behavioral Assays

Forced Swimming Test

Rats were submitted to the forced swimming test (FST), according the procedure initially described by (Detke et al., 1995) and slightly modified by (Bianchi et al., 2002). Briefly, rats were individually placed into a Plexiglas cylinder (40 cm height, 20 cm diameter) containing 25 cm of water at 25±1° C., under 50 lux illumination. After a pre-test session of 15 min, rats were removed, dried and returned to its housed cage. Twenty-four hours after the pre-test session, rats were still placed in the swim cylinder (under identical conditions) for the 5-min test session. The pre-test and test sessions were recorded using a video camera placed above the cylinder for subsequent behavioral analysis. The immobility time (in sec) was blindly measured by two independent experimenters from recorded videos. Rats were considered as immobile when none activity was observed other than that required to keep the rat's head above the water.

Elevated-Plus Maze

We used the elevated-plus maze (EPM) as an assay of anxiety-related behavior in rodents (Walf and Frye, 2007). Rats were initially placed in the center of the plus-maze, consisting of two open arms (50×10 cm) and two closed arms (50×10 cm enclosed by 40 cm walls), in a 50 lux illuminated room and videotaped during 5 min using a computerized system (VideoTrack V2.5, ViewPoint, Lyon, France). The time spent in the open versus closed arms was blindly measured by two independent experimenters from the recorded video, and the open arm-index was calculated as follow: time in the open arms (sec)/[time in open arms (sec)+time in closed arms (sec)].

Open-Field Arena

The animals were individually placed in the open field arena (OFA) (70×100×70 cm), with a central square (35×50 cm), located in a 50 lux illuminated room and videotaped during 3 min using a computerized system (VideoTrack V2.5, ViewPoint, Lyon, France).

OFA allows firstly the evaluation of total locomotor activity (LMA) thereby measuring the total distance travelled in the arena (in cm). Secondly, measurements of the activity in the center of the arena like (i) the number of entries in the center of arena and (ii) the total time spent in the center of arena (in sec) provide cues of anxiety-like behavior (Prut and Belzung, 2003). All these behavioral parameters were instantaneously measured automatically with the VideoTrack V2.5 software from the videos.

Statistical Analyses

All data are expressed as means±SEM. One-way ANOVA or two-way ANOVA were used to detect statistical significance of dependent variables. The Fisher's LSD test was then employed as post-hoc test to compare means from each group. All tests were performed using Graphpad Prism software. Differences between groups were considered significant at the 95% confidence level ($p \le 0.05$).

Results

Anxiodepressive-Like State in WKY Rats

Locomotor Activity

Figure 4A:
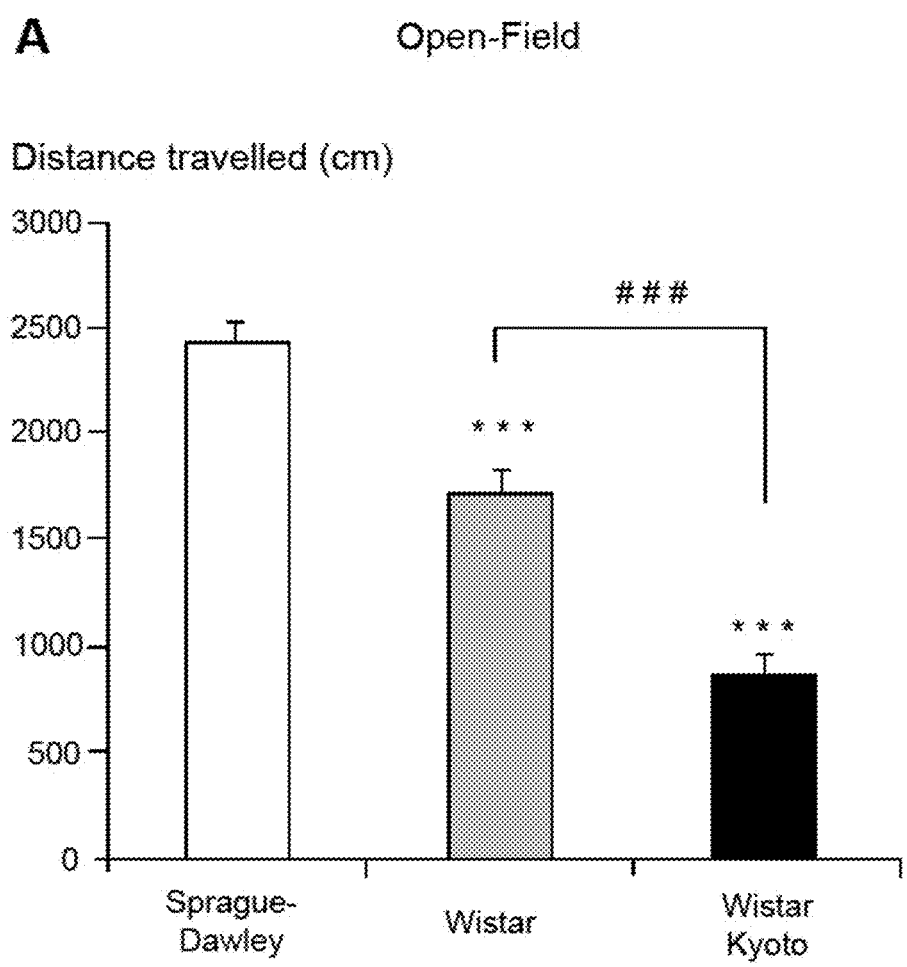
FIGS. 4A, 4B, 4C, 4D, 4E. Characterization of the anxiodepressive-like behavior of WKY rats.

Total locomotor activity (LMA) was measured in the OFA during 3 minutes. A significant difference in LMA was found according to the rat strains ($F_{2,39}=57.02$; $p<0.001$): WI rats displayed a reduced total distance travelled in the arena (−29%; $p<0.001$) when compared to SD rats, while in WKY rats, the reduction of LMA was more pronounced (−64% and −50% when compared to SD and WI rats respectively, $p<0.001$) (FIG. 4A).

Anxiety-Like Behavior

Figure 4B:
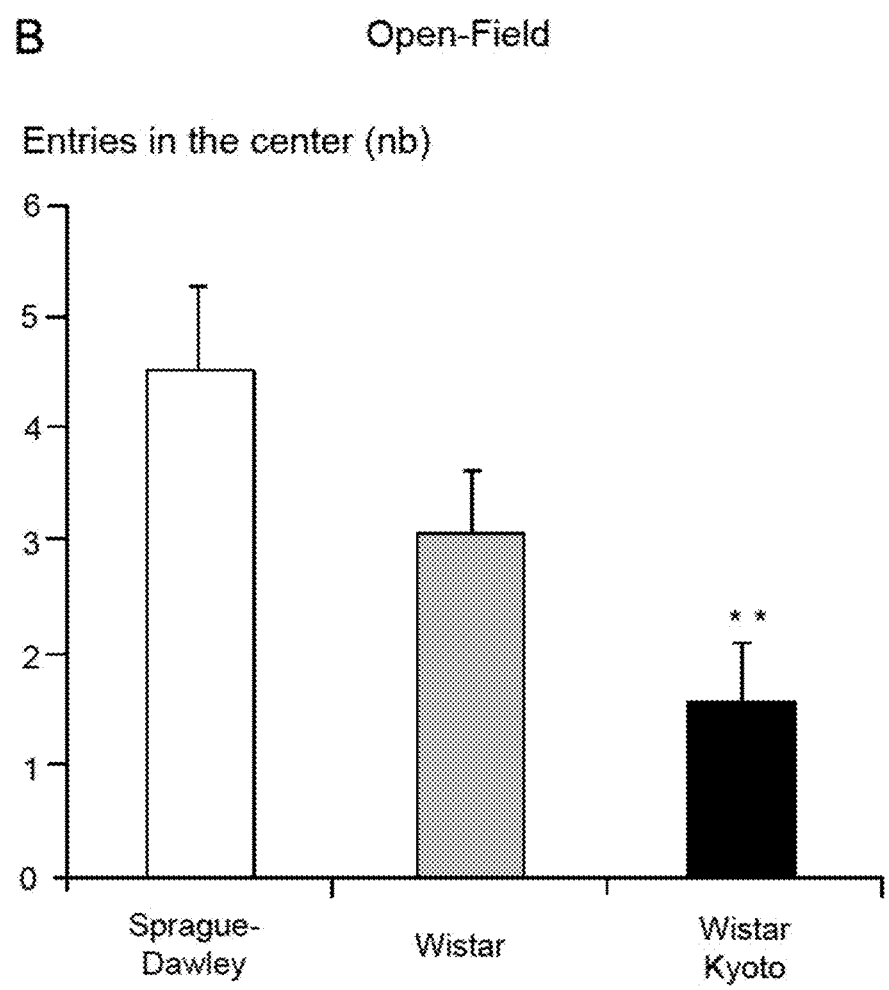

Activity in the Center of the OFA:

Statistical analyses revealed a significant effect of strain rat on the number of visits in the central square of the open-field arena ($F_{2,39}=3.98$; $p<0.05$, one-way ANOVA, FIG. 4B), and WKY rats showed a significant reduction of the number of entries in this area of −65% when compared to SD rats ($p<0.01$) and −59% when compared to WI rats ($p<0.05$).

Figure 4C:
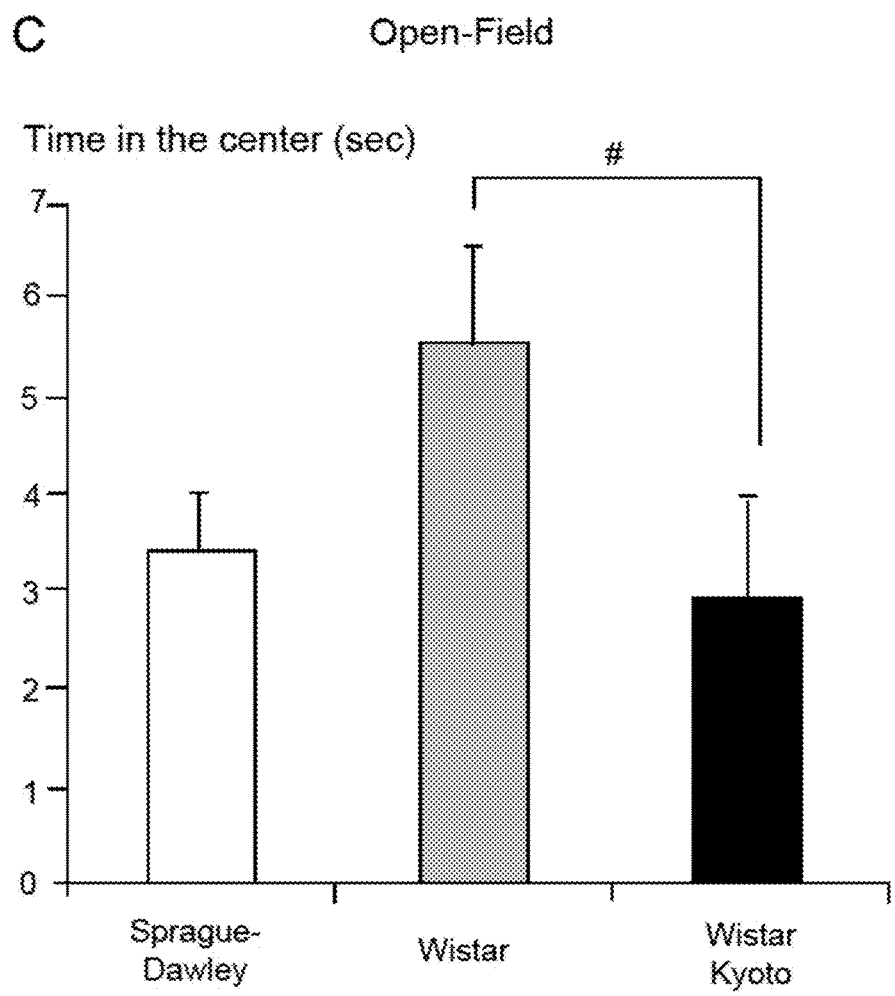

The time spent in the center of the arena was not found significantly different according the three rat strains considered ($F_{2,38}=2.33$; $p=0.11$, one-way ANOVA, FIG. 4C), although a significant reduced time was found in WKY when compared to WI rats (−47%; $p=0.05$; FIG. 4C).

Figure 4D:
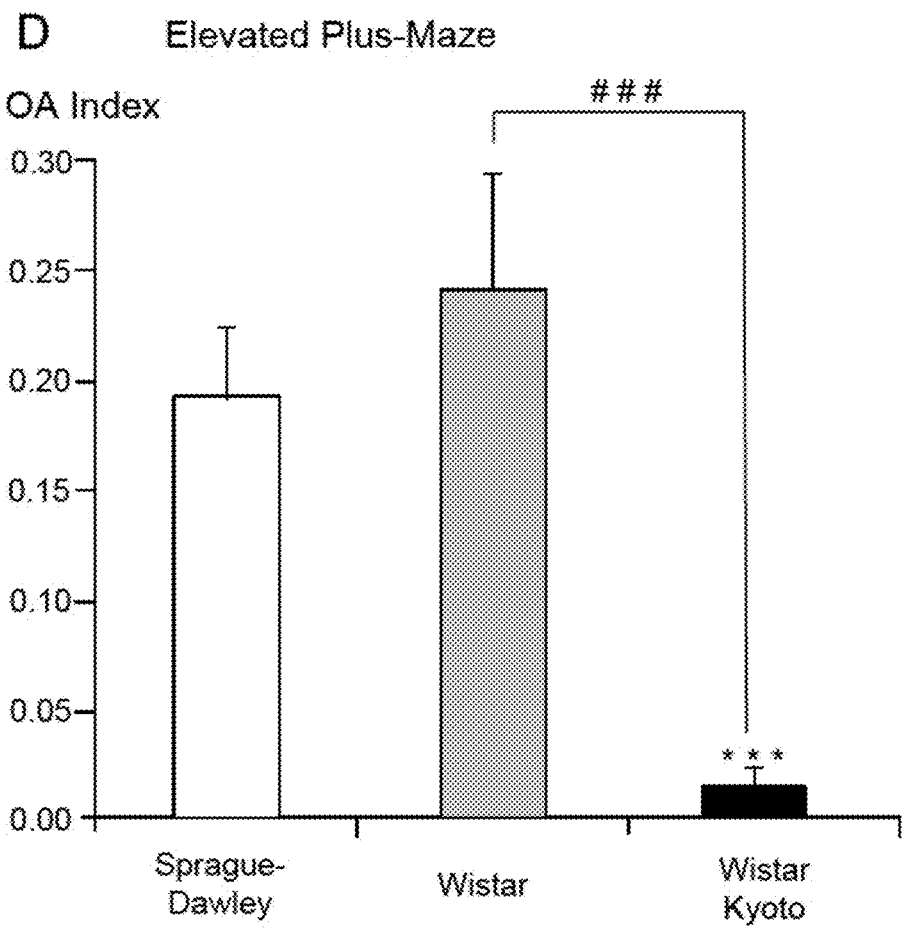

EPM Test:

Statistical analysis of data obtained in EPM revealed a significant effect of strain on the OA index ($F_{2,39}=11.13$; $p<0.001$; one-way ANOVA, FIG. 4D). While SD and WI rats exhibited a similar OA index, WKY rats spent a drastic reduced time in open-arms as compared to SD (−91%, $p=0.01$) or WI rats (−93%, $p<0.001$), respectively.

Depressive-Like Behavior in FST

Figure 4E:
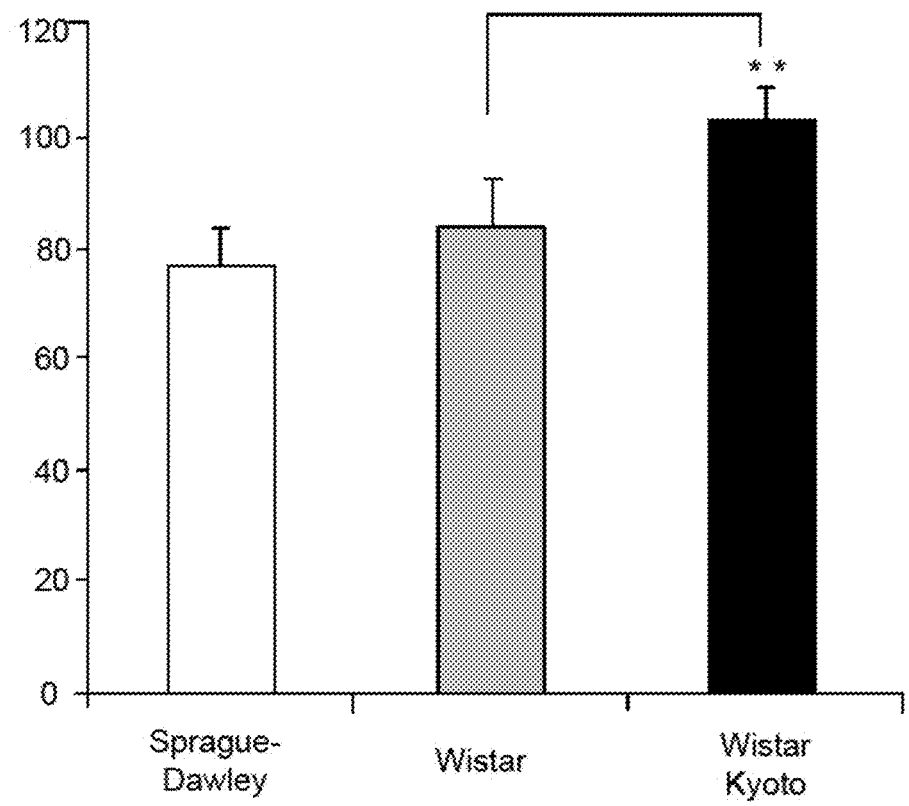

Statistical analysis of data obtained in FST showed a significant effect of strain on the immobility time ($F_{2,32}=3.34$; $p<0.05$; one-way ANOVA; FIG. 4E). Indeed, WKY rats displayed an increased immobility as compared to SD rats (+34%, $p<0.05$). When compared to WI rats, the immobility time of WKY rats was also increased in WKY but not significantly (+23%, $p=0.08$).

Acute administration of MAP4343 reverses anxiodepressive-like behavior in WKY rats: comparison with fluoxetine and ketamine MAP4343 Plasma Concentrations WKY rats treated with MAP4343 displayed measurable plasma levels of MAP4343, which reached 40.1±2.5 ng/ml (121±7.5 nM) after 4 repeated subcutaneous injections.

Locomotor Activity in the Open-Field Arena

Figure 5A:
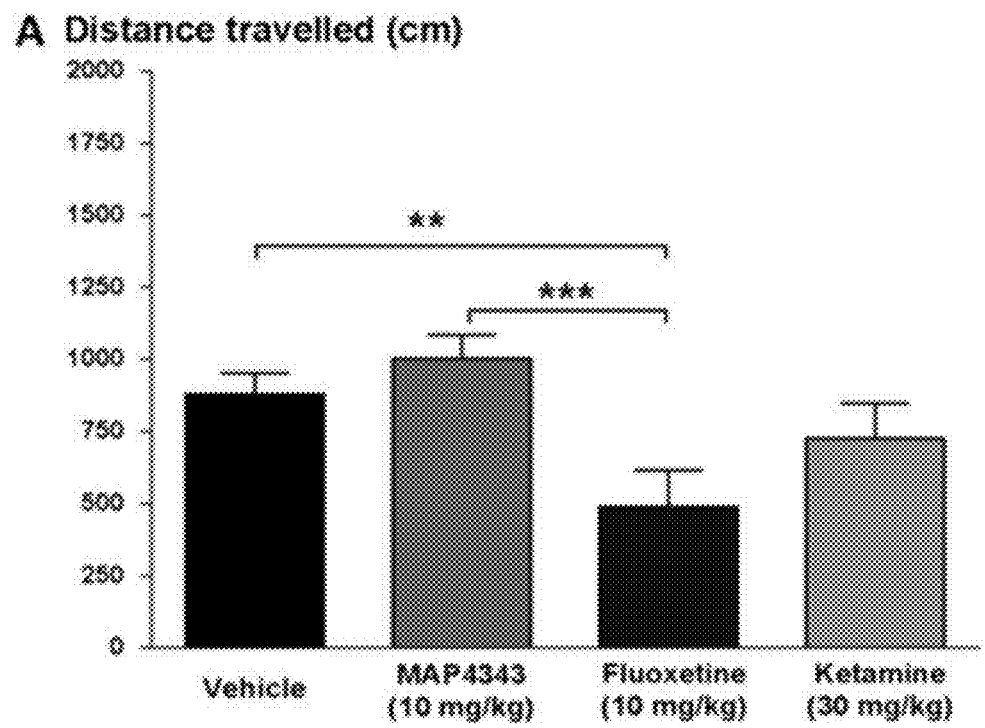
FIGS. 5A, 5B, 5C, 5D. Effects of MAP4343 on anxious like behavior of WKY rats: comparison with fluoxetine and ketamine.

Statistical analysis showed a significant effect of treatments on the total distance travelled in the open-field arena ($F_{3,56}=5.08$; $p<0.01$. one-way ANOVA). An acute injection of MAP4343 (10 mg/kg, s.c.) in WKY rats did not modify significantly the locomotor activity as compared to that measured in WKY receiving vehicle, $p=0.31$; FIG. 5A). In contrast, fluoxetine administration (10 mg/kg, i.p.) significantly reduced the locomotor activity as compared to either WKY receiving vehicle (−45%, $p<0.01$) or MAP4343-treated WKY (−52%, $p<0.001$; FIG. 5A). WKY treated by ketamine (30 mg/kg, i.p.) displayed no significant change of locomotor activity as compared to WKY receiving vehicle or to MAP4343-treated WKY.

Anxious-Like Behavior

Figure 5B:
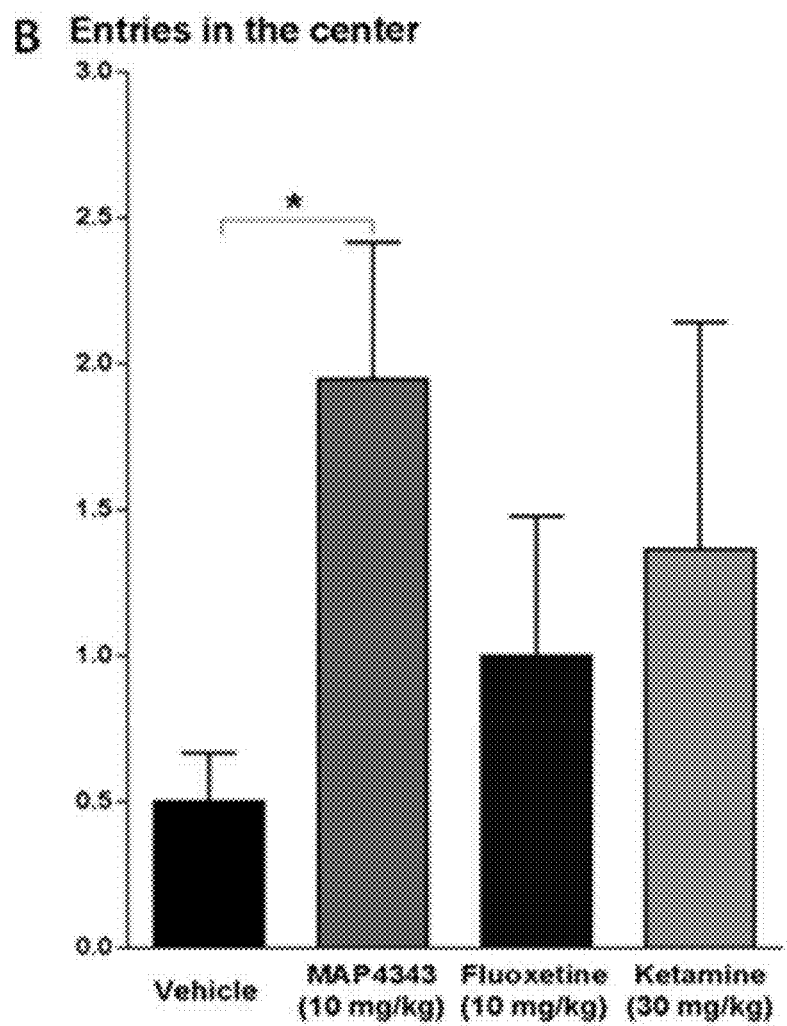

Activity in the Central Square of the OFA:

The number of entries in the central square of OFA was not significantly affected by the various treatments in WKY ($F_{3,56}=2.09$; $p=0.11$, One-way ANOVA). However, a significant increase of entries (+289%, $p<0.05$) was found in WKY treated with MAP4343 (10 mg/kg, s.c.) as compared to WKY receiving only vehicle (FIG. 5B). By contrast, acute administration of fluoxetine (10 mg/kg, i.p.), as well as ketamine (30 mg/kg, i.p.), failed to significantly modify the low entries in the center observed in WKY rats.

Figure 5C:
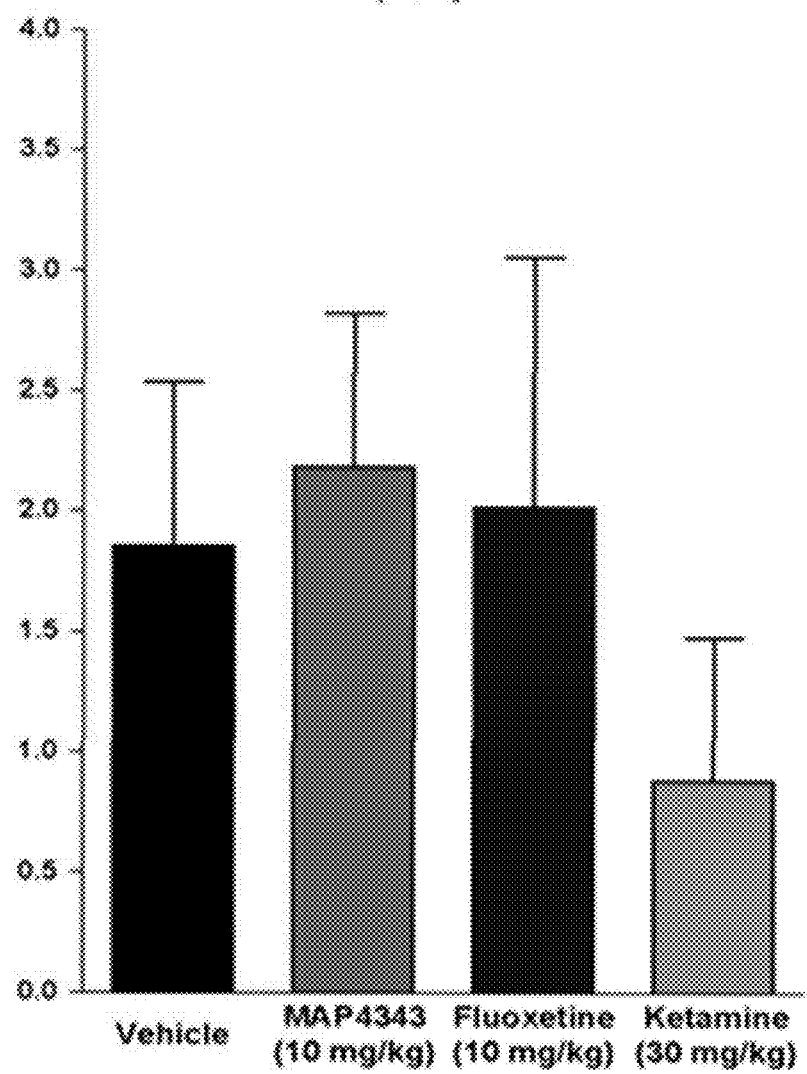

Measurements of the time spent in the center of open-field revealed no significant effect of treatments in WKY rats ($F_{3,55}=0.47$; $p=0.69$, One-way ANOVA; FIG. 5C). Hence, the acute administration of MAP4343 (10 mg/kg, s.c.) did not modify the low time spent in central square of arena in WKY receiving vehicle (p=0.72). Similarly, fluoxetine (10 mg/kg, i.p.) or ketamine (30 mg/kg, i.p.) administration did not induce any significant change of this measure (p=0.88 and p=0.39 for fluoxetine- and ketamine-treated WKY, respectively, when compared animals receiving only vehicle; FIG. 5C).

Figure 5D:
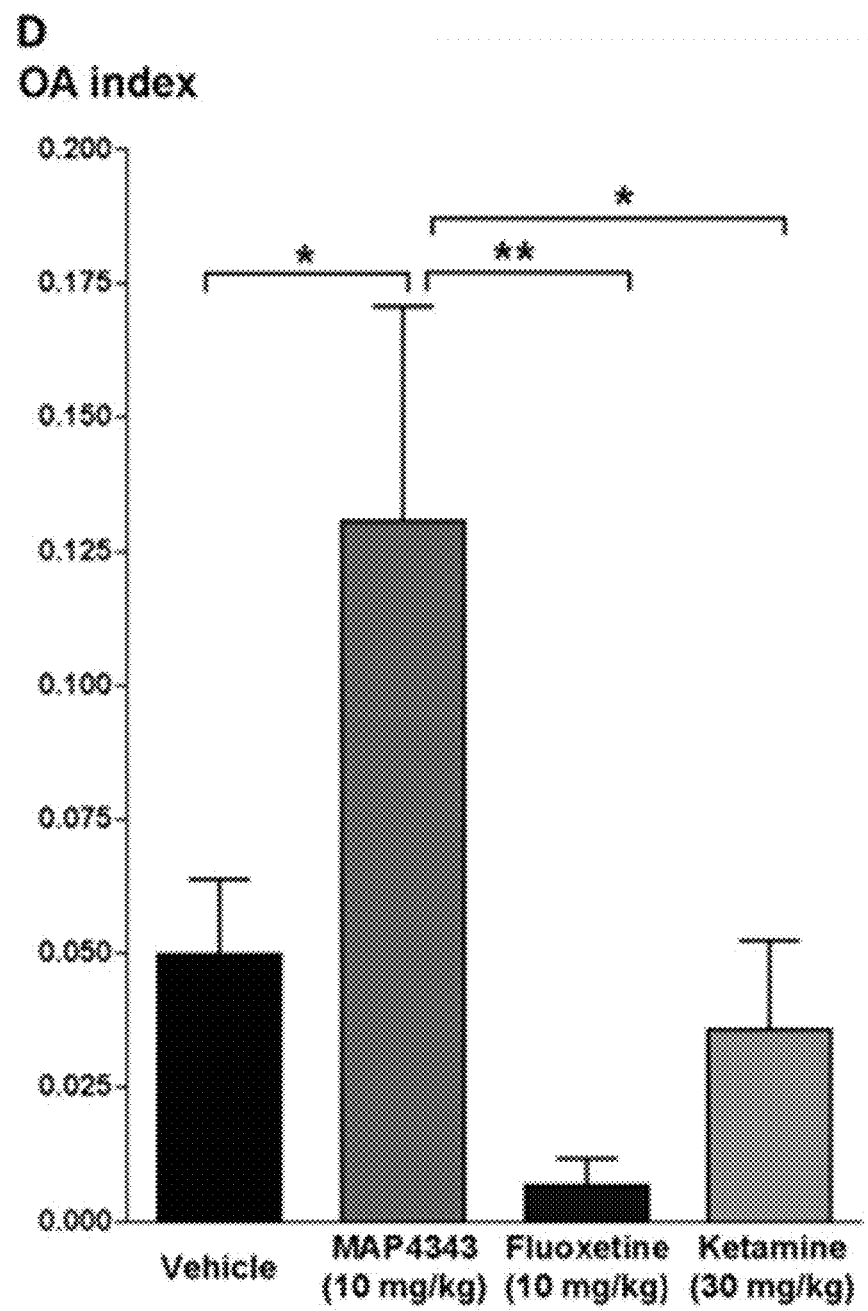

Activity in Open-Arms of EPM:

A significant effect of treatments on the open-arm (OA) index, that corresponds to the percent of time spent in the open arms, was observed in WKY ($F_{3,62}$=4.34; p<0.01, One-way ANOVA; FIG. 5D). Interestingly, acute administration of MAP4343 (10 mg/kg, s.c.) significantly increased the OA index by 165% (p<0.05) when compared to WKY receiving vehicle alone (FIG. 5D). On the contrary, acute administration of fluoxetine (10 mg/kg, s.c.) decreased the OA index when compared to animals receiving vehicle (−84%, p=0.24). This decrease became highly significant when compared to MAP4343-treated WKY (−95%, p<0.01). When WKY rats were treated with ketamine (30 mg/kg, i.p.), no significant change of the OA index was observed, as compared to WKY receiving vehicle alone (−29%, p=0.72).

Depressive-Like Behavior in FST

Figure 6A:
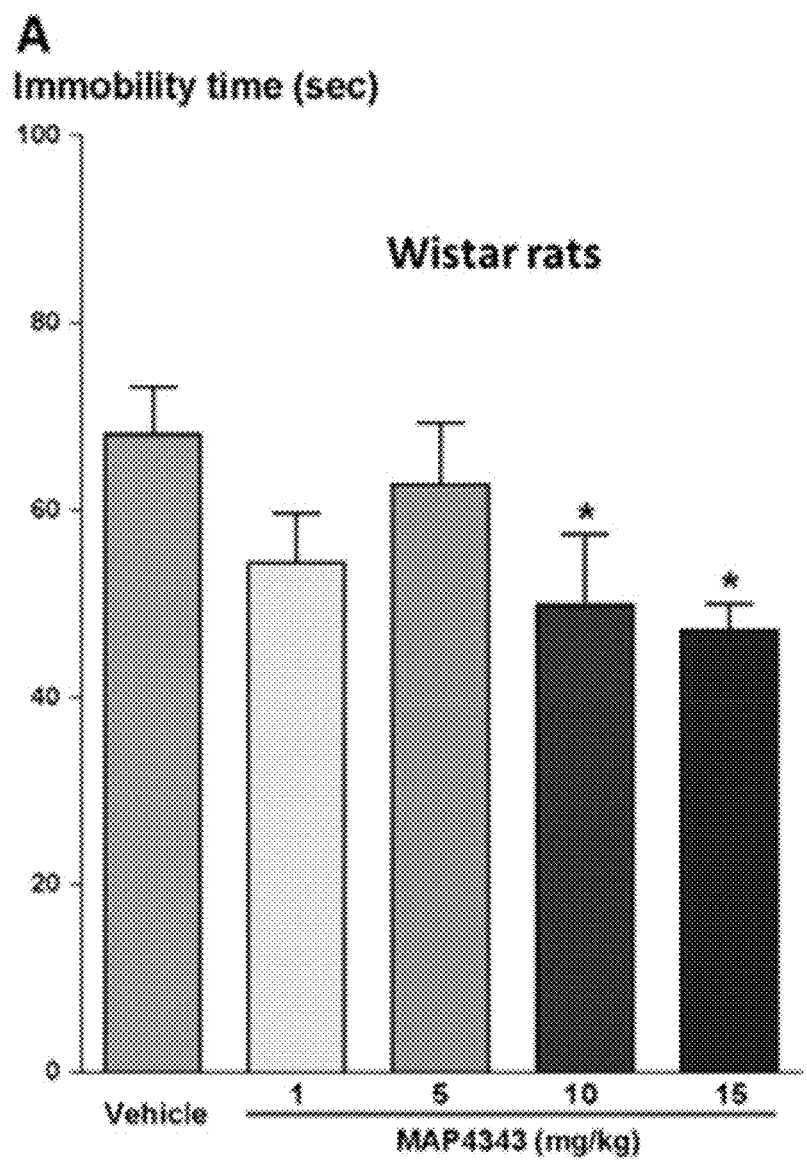
FIGS. 6A, 6B, 6C. Antidepressant-like efficacy of MAP4343 in WKY rats: comparison with fluoxetine and ketamine.

Dose-Ranging in WI and WKY Rats:

The effects of a dose-ranging administration of MAP4343 were tested in WI and WKY rats on their immobility time measured in FST. The two-way ANOVA revealed a significant effect of strain ($F_{1,64}$=6.07; p<0.05) and a significant effect of treatment for each strain ($F_{4,64}$=3.12; p<0.05), whereas no significant interaction strain X treatment was observed ($F_{4,64}$=0.82; p=0.51). In WI rats, the dose-ranging administration of MAP4343 induced a dose-dependent reduction of immobility time measured in FST (FIG. 6A). This decrease was found significant at the doses of 10 mg/kg (−27%) and 15 mg/kg (−31%), respectively (p<0.05 as compared to WI receiving vehicle alone, Fisher's LSD test).

Figure 6B:
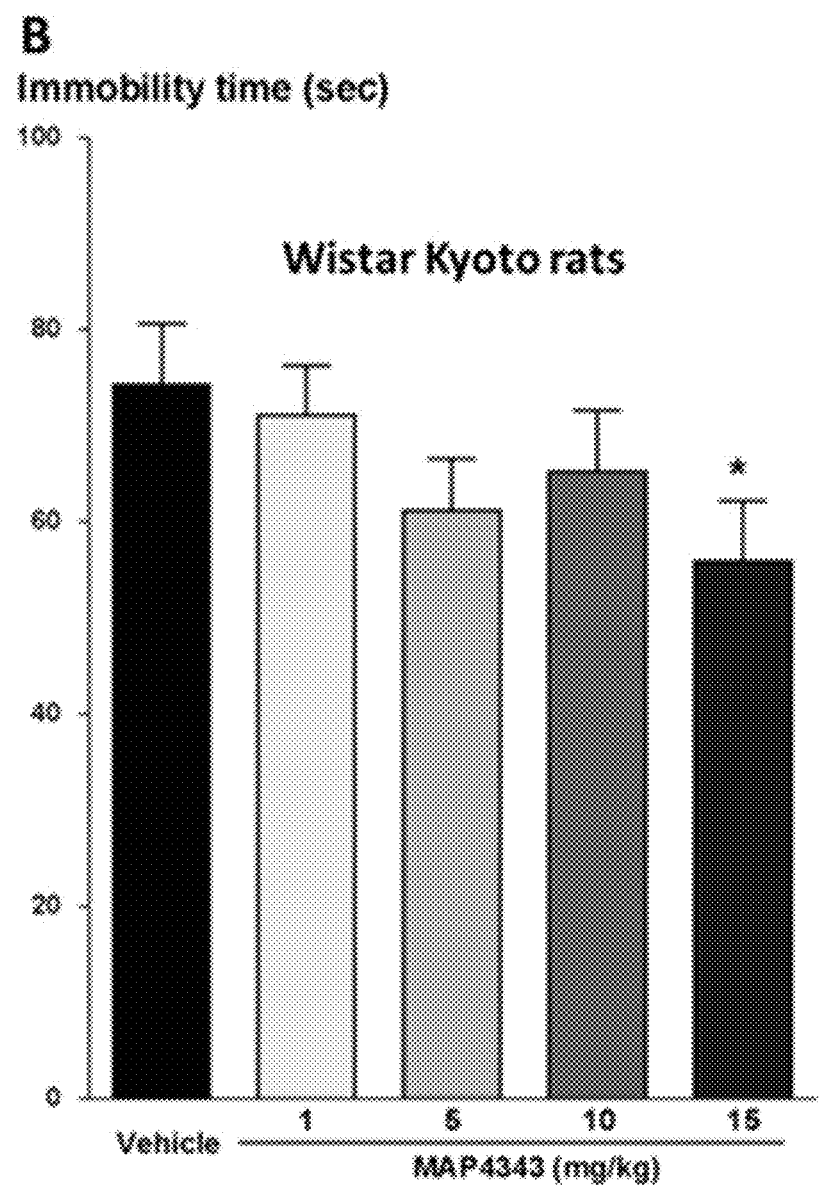

In WKY rats, the dose-ranging administration of MAP4343 also induced a dose-dependent decrease of immobility time measured in FST (FIG. 6B), but this effect was found significant only at the dose of 15 mg/kg (−25%) p<0.05 as compared to WKY receiving vehicle alone, Fisher's LSD test).

Figure 6C:
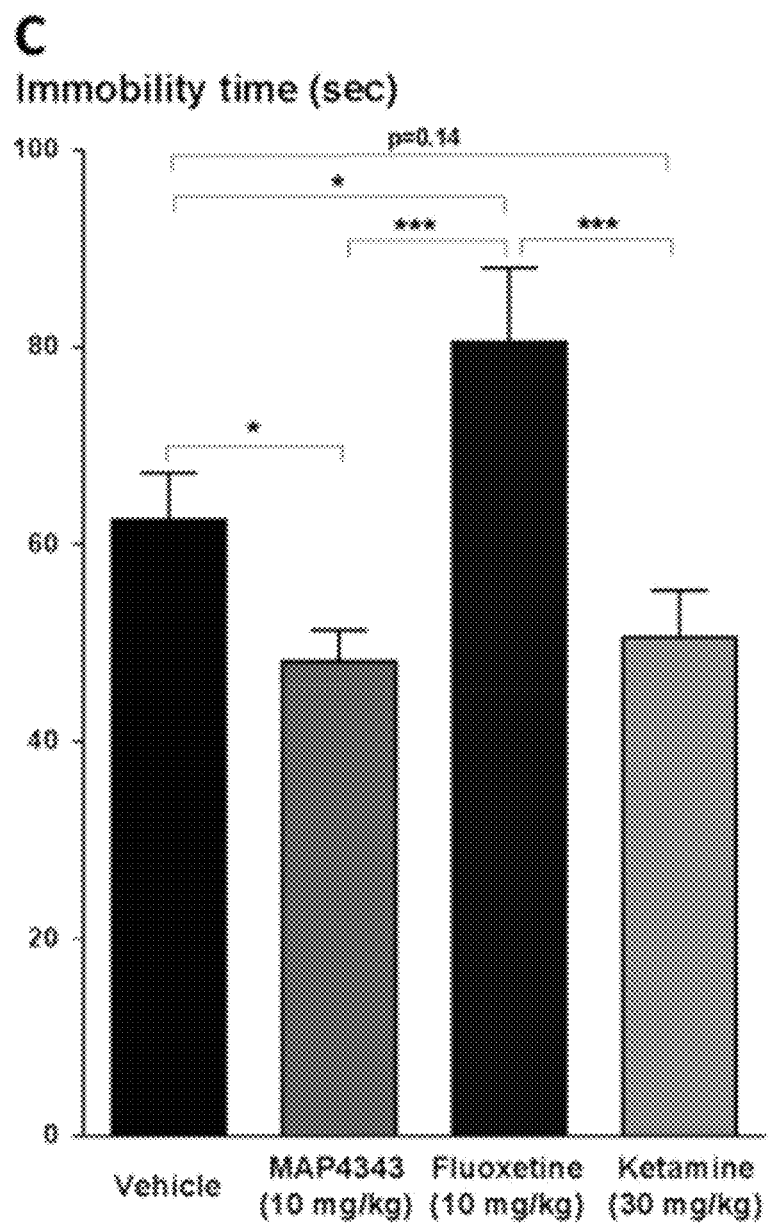

Comparison with Fluoxetine and Ketamine:

A significant effect of various treatments on the immobility time measured in FST was observed in WKY ($F_{3,58}$=7.91; p<0.001, One-way ANOVA; FIG. 6C). Acute administration (4 days) of MAP4343 induced a significant reduction the time of immobility when compared to WKY rats receiving vehicle alone (−23%, p<0.05), whereas treatment fluoxetine (10 mg/kg, i.p.) significantly increased the immobility time (+29%, p<0.05 when compared to WKY receiving vehicle alone). The increased effect of fluoxetine on immobility time appeared highly significant when compared to WKY treated with MAP4343 (p<0.001). Similarly to MAP4343, administration of ketamine (30 mg/kg, i.p.) decreased the immobility time (−19%), but not significantly (p=0.2 when compared to WKY receiving vehicle), contrary to MAP4343 administration.

Conclusions

This study aimed at further demonstrating the antidepressant-like efficacy of MAP4343 using the WKY rat strain, considered as a spontaneous rat model of anxiodepressive disorders (Jiao et al., 2011). In addition, this rat strain displayed a resistance to SSRIs efficacy evidenced in forced swimming test (Griebel et al., 1999; Lopez-Rubalcava and Lucki, 2000), that provide a relevant model of treatment resistance depression (TRD) (see Willner and Belzung, 2015).

The anxiodepressive-like behavior of WKY was first characterized by comparing it to either WI rats to SD rats, taken as control strains. Findings indicated subtle differences between SD and WI rat strains mainly characterized by a decreased LMA in WI rats. WKY rats, initially developed as normotensive control strain for the SHR rats (Okamoto and Aoki, 1963) displayed a severe reduced LMA in OFT when compared to either SD or WI rats, as already described by numerous studies (Jiao et al., 2011), although significant differences into WKY strain were detected according vendors (Pare and Kluczynski, 1997). Such hypolocomotion is not relied on motor disturbance since WKY rats exhibited normal LMA in running wheel (Ferguson and Cada, 2003) or rotarod (Ferguson et al., 2003), and reveals rather the anxious-like behavior of WKY rats. Further behavioral investigations exhibited a clear-cut anxiodepressive phenotype of WKY rats. The specific assessment of anxious-like behavior in two distinct behavioral assays indicated that WKY displayed lower entries and time spent in the center of the arena of OFT, accompanied with lower time spent in the open arms of the EPM. These results confirmed that WKY rats displayed a stronger anxious-like state, as already shown by similar behavioral studies (Durand et al., 1999; Durand et al., 2003). In addition, specific evaluation of depressive-like behavior revealed that WKY rats exhibited an increased time of immobility in FST, similarly to that initially described by Paré and colleagues (1994). Hence, it was confirmed here that WKY rat can be taken as model of anxiodepressive disorders regarding its behavioral responses in validated behavioral test assessing respectively anxious- and depressive-like behavior. Various studies have indicated that the altered behavior of WKY rats was accompanied by physiological disturbances, including exaggerated neuroendocrine response to stress regimens, altered sleep patterns (Dugovic et al., 2000), or lower basal serotonin content in brain regions (Scholl et al., 2010). Finally cellular and molecular changes, very similar as that observed in depressed patients, was described in WKY rats (reduced hippocampal volume and impaired synaptic plasticity (Cominski et al., 2014) and lower expression of brain derived neurotrophic factor (Hauser et al., 2011).

Effects of acute MAP4343 administration were tested on WKY rat behavior. The efficacy of our compound was compared to fluoxetine at classical antidepressant dose for rats (Durand et al., 1999). For MAP4343, the dose of 10 mg/kg of was considered according the dose response previously established in FST with naive SD rats (Bianchi and Baulieu, 2012). Moreover, treatments were administered for 4 days, 1 h 30 before each behavior assay, a similar regimen as previously managed to restore depressive-like phenotype induced by isolation rearing in SD rats (Bianchi and Baulieu, 2012). Here, we observed that acute injection of vehicle in WKY rats did not significantly modify their behavioral measurements, which were found very similar to those observed in naive WKY rats (i.e. reduced body weight, decreased LMA, less entries and time spent in the center of the arena and reduced OA index in the EPM) except for the increased immobility time in FST found not significant in comparison to WI rats. Interestingly, MAP4343 treatment exhibited psychoactive properties in WKY rats which consisted in reducing the anxiodepressive-like behavior of this rat strain. Hence, MAP4343 allowed increasing (i) the spontaneous locomotor activity, (ii) entries and time spent the center of arena in OFT, that suggest its anxiolytic-like efficacy in rats. Finally, MAP4343 diminished the immobility in the forced swimming test, showing its antidepressant-like efficacy as previously suggested in two different animal models of DDs (Bianchi and Baulieu, 2012; Paresys et al. 2015).

When compared to behavioral effects of MAP4343, fluoxetine displayed quasi-opposite effects which consisted in a reduced body weight, a reduced spontaneous locomotor activity, an almost abolished OA index in EPM, and finally an increased immobility time in FST. We further demonstrated here that WKY rats are resistant to fluoxetine, in agreement with literature showing that either acute or chronic administration in WKY rats had no efficacy in OFA (Durand et al., 1999), in EPM (Durand et al., 1999) and in FST (Griebel et al., 1999; Lopez-Rubalcava and Lucki, 2000). Such resistance was also described for acute administration of citalopram (Pollier et al., 2000), as well as for sub-chronic administration (12 days) of paroxetine (Tejani-Butt et al., 2003), i.e. for two other SSRIs. By contrast, desipramine, a tricyclic antidepressant drug, was found efficient to reverse depressive-like behavior in FST (Carr et al., 2010; Pare and Redei, 1993; Tejani-Butt et al., 2003), despite one study did not reproduce such result (Lahmame et al., 1997). Other antidepressant drugs tested in WKY rats have displayed subacute efficacy to reduce immobility in FST, like the monoamine oxidase inhibitor phenelzine (Will et al., 2003); the substance P receptor antagonist [D-Arg$^1$, D-Phe$^5$, D-TRP$^{7,9}$, Leu$^{11}$], although this latter efficacy was found very slight (Malkesman et al., 2007), or the NMDA receptor antagonist, ketamine (Tizabi et al., 2012).

Ketamine was used for its rapid antidepressant efficacy, evidenced in patients suffering from major depression (Berman et al., 2000), and treatment-resistant major depression (Zarate et al., 2006). In rodents, a single injection of ketamine produced an antidepressant-like effect (Garcia et al., 2008), which persists during several days after the administration (Yilmaz et al., 2002). As previously mentioned, ketamine elicited antidepressant-like effect in WKY after either acute or chronic (10 days) administration of low dose of ketamine (2.5 and 5.0 mg/mg) (Tizabi et al., 2012). A concomitant study from the same group reported that the antidepressant-like efficacies of low doses of ketamine, observed in FST, were potentiated by the co-administration of AMPA (Akinfiresoye and Tizabi, 2013). Here, we found only a slight effect of ketamine at 30 mg/kg to reduce the immobility time of WKY in FST, contrasting with the precedent studies from Tizabi and colleagues. In two tests (immobility in FST and OA index in EPM), MAP4343 was found to be superior to ketamine.

Here, we found that MAP4343 exert a rapid efficacy to directly reverse both anxious-like and depressive-like behavior. Such of complete psychoactive profile associating both anxiolytic and antidepressant properties, was never described for other drugs already tested in WKY rats. Taken together, our results reinforce the demonstration of the antidepressant-like efficacy of MAP4343 using this TRD model.

Example 5: Other Molecules According to the Invention

The indices of binding and activity are expressed as a percent of pregnenolone (PREG).

Binding (affinity) is measured by the displacement of PREG-$^3$H.

Activity is measured by the increase in optical density at 345 nm of a mixture of purified tubulin and MAP2, incubated at 37° C. in the presence of GTP.

Stimulation of neuritic sprouting is conducted on PC12 cells differentiated in the presence of NGF (10 ng/ml) and the steroid being tested (30 µM) for 3 days. For each condition, the average length of the longest 200 neurites in each cell is measured simultaneously for 3 cultures.

The results are represented in Table 5 below by one, two or three crosses (+) according to whether stimulation is lower than, equal to, or higher than that produced by PREG.

TABLE 5

Indices of binding and activity of other molecules, expressed as a percent of PREG

| Steroid | Affinity | Activity | Neuritic sprouting |
|---|---|---|---|
| Pregnenolone (PREG) | 100 | 100 | ++ |
| 3β-methoxy-pregna-5-ene-20-one (3-methoxy-PREG) | 100 | 100 | +++ |
| 3β-methoxy-pregna-5-ene-20-one-17α-dichloromethyl | 53 | 113 | +++ |
| 3β-methoxy-5α-pregnane-20-one | 87 | 10 | +++ |
| 3β-methoxy-5α-pregnane-20β-ol | 65 | 65 | ++ |
| 3β-methoxy-pregna-5,14-diene-20-one | 102 | 50 | + |
| PREG-16α-methyl | 80 | 70 | ++ |
| PREG-16β-methyl | 63 | 67 | (++) |
| PREG-16α,17α-epoxy | 41 | 54 | + |
| PREG-16α,17α-methylene | 62 | 49 | + |
| Pregna-5-ene-3β, 20β-diol-20-acetate | 60 | 108 | ++ |
| 3β-hydroxy-5α-pregnane-20-one-16α-methyl | 57 | 53 | (+) |

These results show the effectiveness of other molecules derived from pregnenolone to stimulate the polymerization of microtubules induced by MAP2 and to stimulate neuritic sprouting. It may thus be expected that these derivatives or their 3β-methoxy-derivatives (which will not be converted to progesterone in vivo) will maintain the activity of 3β-methoxy-pregna-5-ene-20-one (3β-methoxy-PREG).

Figure 7:
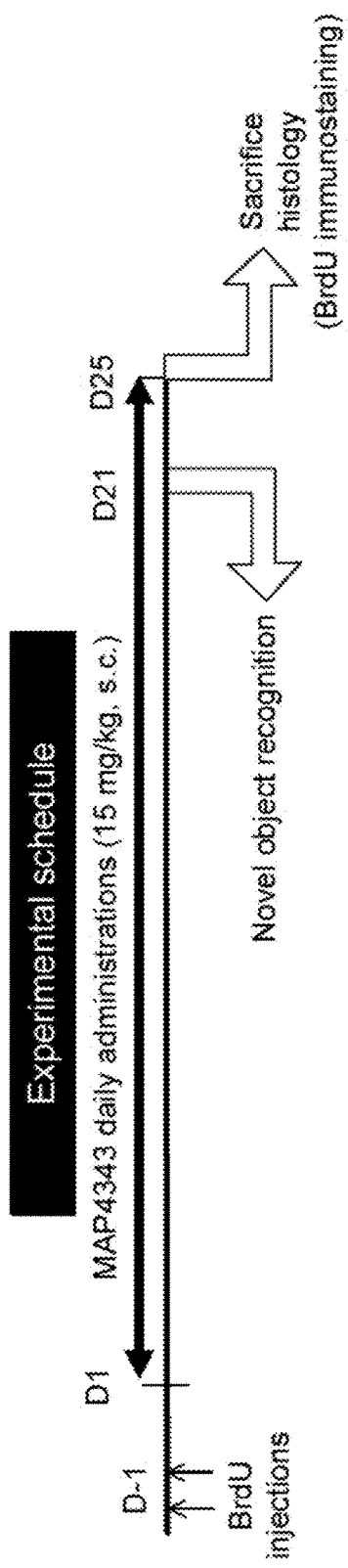
FIG. 7. Experimental schedule including MAP4343 administration, the novel object recognition (NOR) test and the neurogenesis analysis with BrdU immunostaining.

Example 6: Effects of Chronic Administration of MAP4343 (15 mg/kg) on Cognitive Performance and Neurogenesis in Wistar Kyoto Rats Material and Methods
Experimental Design Wistar Kyoto (WKY) rats are considered as a model of treatment-resistant depression, while Wistar (WI) rats are used as control strain of WKY rats. During this experiment both WI and WKY rats were administered with MAP4343 (15 mg/Kg), subcutaneously (s.c.) for 24 days. Behavioral tests were performed at during the last week of treatment, and rats were finally sacrificed for addressing neurogenesis in Gyrus dentate of hippocampus using histological experiments. Organization of this protocol is depicted in FIG. 7.

Animals

All animals (WI and WKY male rats from Harlan Laboratories, 7 weeks of age) were housed in groups of three or four per cage under controlled conditions of a standard 12 h light/12 h dark cycle, 22° C. and had free access to food and water. All animals had one week of acclimatization before the beginning of any treatment or experiment.

Drug Administration

MAP4343 was diluted in sesame oil, and then administered subcutaneously (s.c.) at the dose of 15 mg/kg during 24 days. The vehicle group received only the sesame oil (1 ml/kg) in the similar conditions.

Novel Object Recognition (NOR)—Cognition and Memory

The NOR task is a test of recognition memory based on the spontaneous preference of rats for novelty. The applied procedure was based on that previously described by Ennaceur and Delacour (1988). NOR task was performed at D21 of the treatment period (see FIG. 7). In a first session (habituation, 5 min), each rat was familiarized with two identical objects placed in the border of the open-field area (70×100×70 cm). In a second session performed 1 h after (novel object recognition, 5 min), one of the two familiar objects was replaced by a novel object. Exploration time (duration when each rat displays an interest for one object) for each object was measured. Results are given as exploratory time for the novel object and the total exploratory time.

Histology of Neurogenesis

Bromodeoxyuridine Labeling

Injections of BrdU were performed twice at D0, 24 and 22 hours before the beginning of treatment. All animals were equally given two injections of BrdU (75 mg/kg, dissolved in saline solution intraperitoneally), at two hours pulse-chase interval.

Sacrifice and Brain Collection

Animals were anesthetized with pentobarbital (80 mg/kg, i.p), and two sequences of intracardiac perfusions were performed: the first using PBS (75 mL/rat) to totally remove the blood from tissues, and the second with paraformaldehyde (PFA 4%, 150 mL/rat) to fix tissues. Entire brains were then removed and placed in tubes filled with PFA 4% for 24 hours, and finally placed in tubes filled with PBS+sodium azide (0.01%) until realization brain free-floating sections.

Free-Floating Sections

Entire brains were placed in small plastic matrixes, and then recovered with liquid agar 3%. After agar solidification, anterior (prefrontal cortex) and posterior (cerebellum) parts were removed with a razor blade to approximately delimit the zone of interest (i.e. the hippocampus). The anterior side was then glued on the vibratome plate (Leica VT1000S), and the whole tissue block was immersed into PBS 1%. Free-floating coronal sections (40 μm) were made from posterior to anterior hippocampus. To obtain all the dentate gyrus (approximately 3.5 mm), a minimum of 96 slices for each brain was collected. Slices were transferred to a 6-well plate filled with cryoprotectant solution (PBS 1×40%, Ethylene Glycol 30%, Glycerol 30%). Sections were stored at −20° C. until immunohistochemistry staining.

Immunohistochemistry

In regard to stereological considerations (West, 1999), immunohistochemistry (IHC) experiments were performed on ⅛th of the obtained sections, for a total of 12 serial sections per animal. Sections were rinsed three times in PBS 1× (5 min each, RT, gentle shaking), then DNA denaturation was performed in HCl 2N+Triton X-100 0.5%, at 37° C. for 30 min. HCl was neutralized in Borax 0.1M for 30 min (RT, gentle shaking). Unspecific sites were blocked with a buffer containing 5% Goat Serum+PBS-Triton 0.1%, and the incubation with the primary antibodies (anti-BrdU monoclonal mouse, Dakocytomation, 1:50, and anti-NeuN polyclonal rabbit, Chemicon, 1:1000; both diluted in the blocking buffer) was performed at 4° C. overnight, on shaker. The day after, sections were rinsed three times in PBS 1× (5 min each, RT, gentle shaking), and then secondary antibodies (Alexa Fluor 488® goat anti-mouse; 1:500, and Alexa Fluor 555® goat anti-rabbit, 1:1000, Invitrogen, both diluted in blocking buffer) were incubated with brain sections during 2 h at RT, under gentle shaking. Sections were finally rinsed five times in PBS 1× (5 min each, RT, gentle shaking), and finally mounted on Superfrost Plus™ slides, using Fluoromount G® mounting medium. All slides dried at least 24 h before observations.

Quantification of Neurogenesis

Neurogenesis in each dentate gyrus was manually measured by quantification of positive cells co-labelled with BrdU/NeuN, using a microscope equipped with epifluorescence (Zeiss Axiovert 200, objective 40×). Total number of new neurons in the entire dentate gyrus was estimated by multiplying the measured number by 8 (that corresponds to the number of unused sections separating each coronal sections used to count the newly-formed neurons). Illustrative pictures have been made with confocal microscope Leica SP8.

All quantitative data are presented as means±SEM and n refers to the number of independent animal used for each experiment. One-way ANOVA was employed to detect differences of variances between groups and was followed, in case of significance by a Fisher's LSD post hoc test to compare means. All tests were performed using Graphpad Prism software. Differences between groups were considered significant at the 95% confidence level ($p \leq 0.05$).

Results

MAP4343 improves cognitive performances in WKY

Figure 8A:
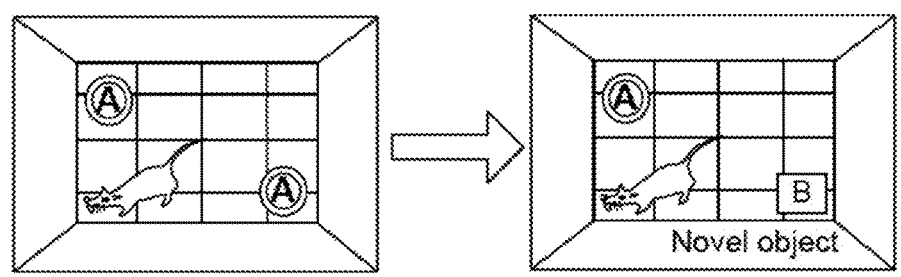
FIGS. 8A, 8B, 8C. MAP4343 (15 mg/kg, s.c., 24 days) improves the cognitive performances of WKY rats, evaluated in novel object recognition (NOR) test.
Figure 8B:
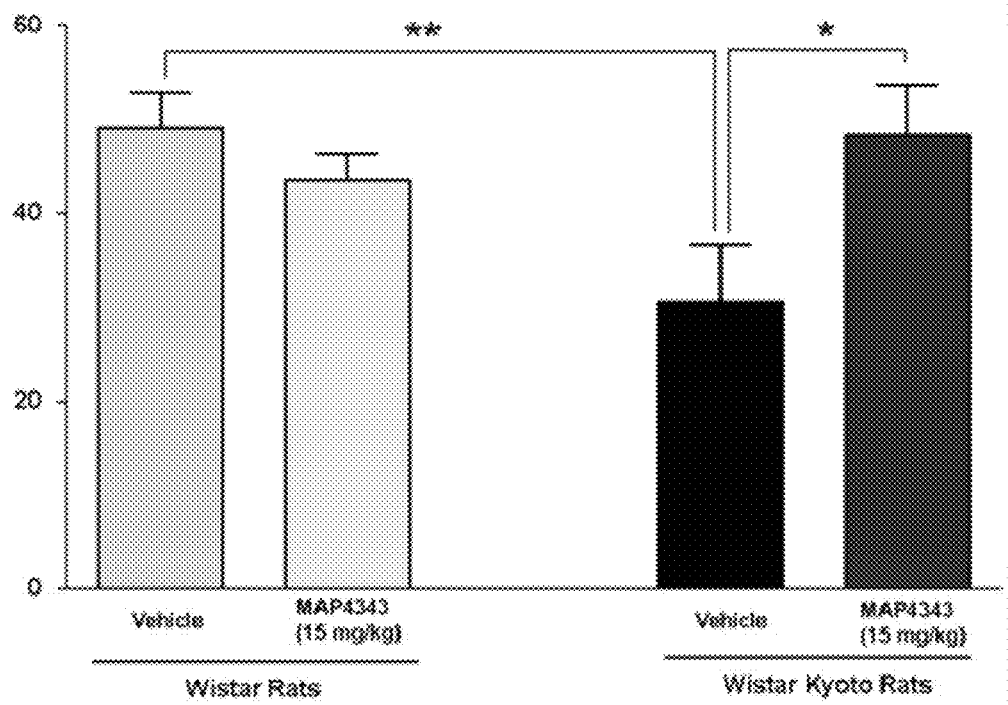
Figure 8C:
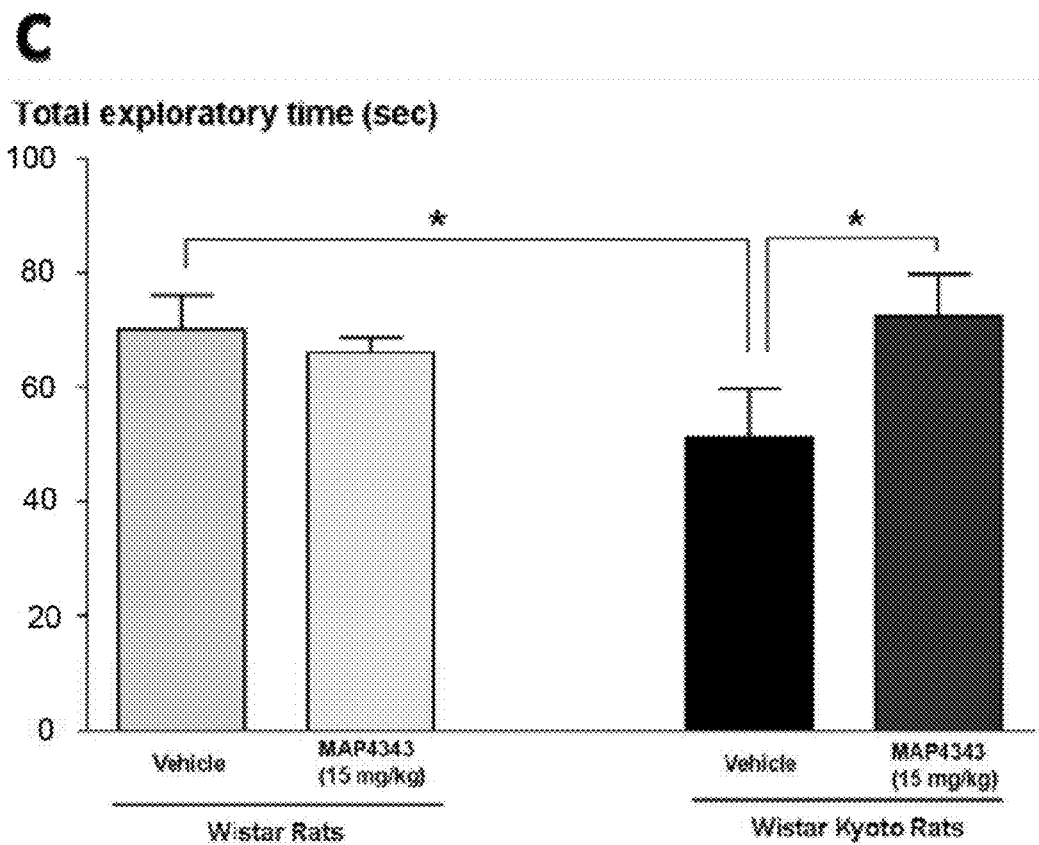

As shown by the FIG. 8A through FIG. 8C, WKY rats display a lower total exploratory time (−27%, $p<0.05$, FIG. 8C) and particularly a lower time to explore the novel object (−38%, $p<0.01$, FIG. 8B), as compared to the WI rats. These results indicate a deficit of cognitive performances to discriminate a novel object in WKY rats.

Interestingly, the long-term administration of MAP4343 (15 mg/kg, s.c., 24 days) in WKY rats allows a total recovery of cognitive deficits, since the total exploratory time, as well as the time spent with the novel object, are significantly raised as compared to WKY rats receiving only vehicle (+41% in FIG. 8C and +58% in FIG. 8B, respectively, $p<0.05$).

Figure 9A:
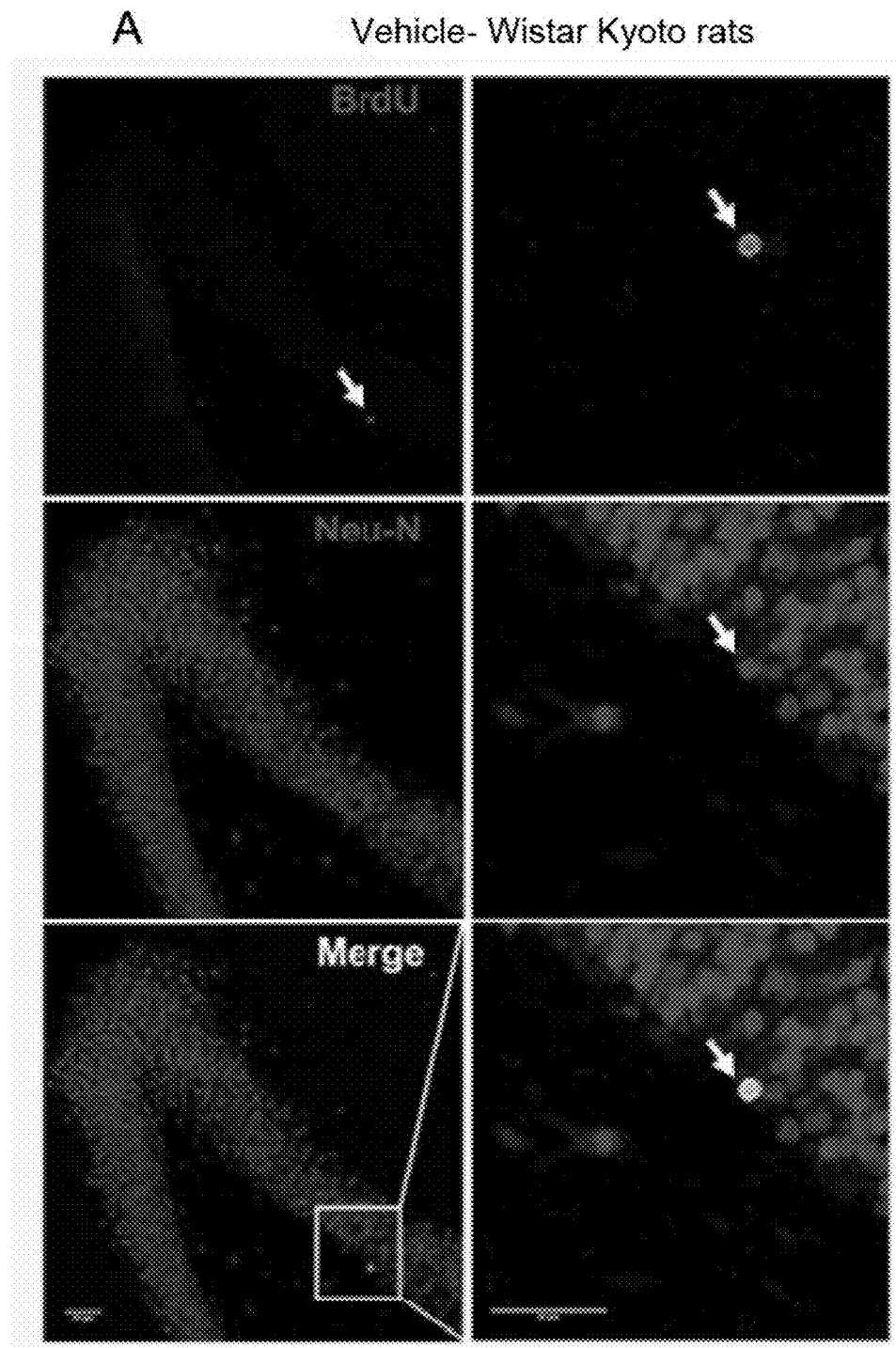
FIGS. 9A, 9B, 9C. MAP4343 (15 mg/kg, s.c., 24 days) increases the number of newly-formed neurons.
Figure 9B:
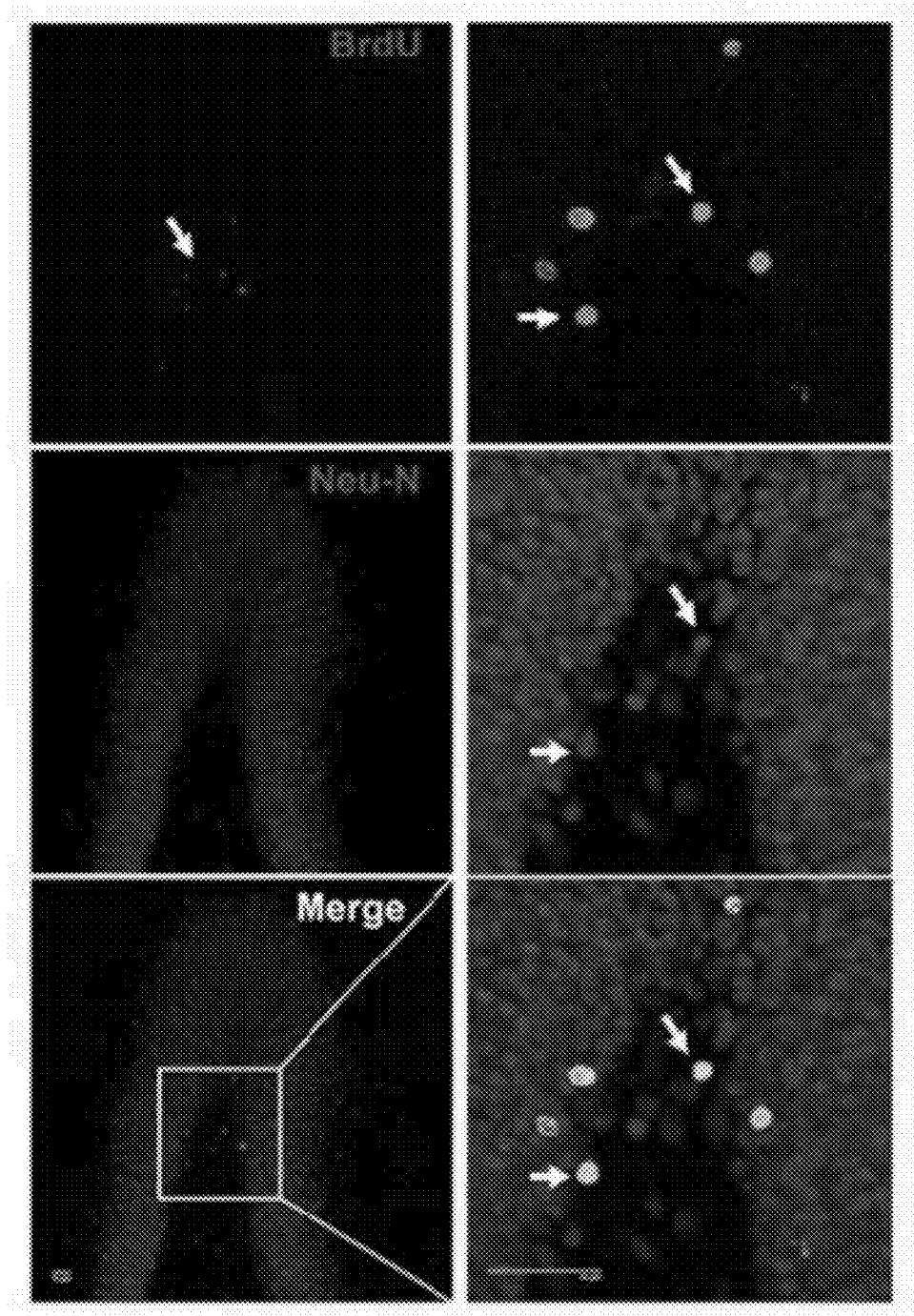
Figure 9C:
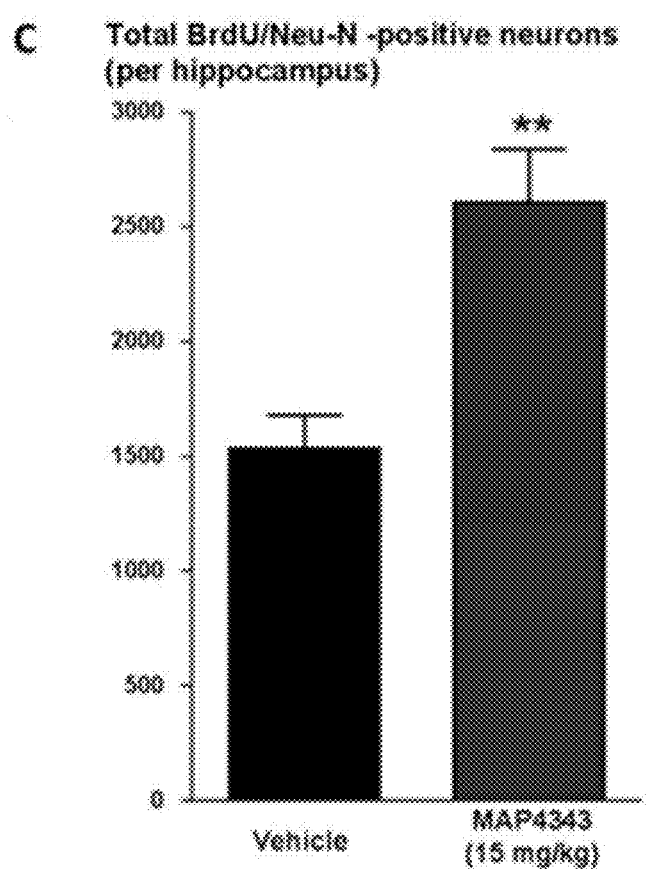

MAP4343 Increases Neurogenesis in Dentate Gyrus of Hippocampus in Wistar Kyoto Rats Quantifications of neurogenesis in the Dentate Gyrus of hippocampus reveal that chronic admin. of MAP4343 in WKY rats significantly increases the number of newly-formed neurons (i.e. cells positively labelled with both BrdU and Neu-N) when compared that observed in WKY receiving only vehicle (+71%, $p<0.01$; FIG. 9C and comparison of FIG. 9A and FIG. 9B).

BIBLIOGRAPHIC REFERENCES

Akinfiresoye, L., Tizabi, Y., 2013. Antidepressant effects of AMPA and ketamine combination: role of hippocampal BDNF, synapsin, and mTOR. Psychopharmacology (Berl) 230, 291-298.

ALONSO J, ANGERMEYER M C, BERNERT S, BRUFFAERTS R, et al. Disability and quality of life impact of mental disorders in Europe: results from the European Study of the Epidemiology of Mental Disorders (ESEMeD) project. Acta Psychiatr Scand Suppl. 2004b; (420):38-46.

ALONSO J, ANGERMEYER M C, BERNERT S, BRUFFAERTS R, et al. Use of mental health services in Europe: results from the European Study of the Epidemiology of Mental Disorders (ESEMeD) project. Acta Psychiatr Scand Suppl. 2004a; (420):47-54.

ANDLIN-SOBOCKI P, WITTCHEN H U. Cost of affective disorders in Europe. Eur J Neurol. 2005 June; 12 Suppl 1:34-8.

Armario, A., Gavalda, A., Marti, J., 1995. Comparison of the behavioural and endocrine response to forced swimming stress in five inbred strains of rats. Psychoneuroendocrinology 20, 879-890.

Berman, R. M., Cappiello, A., Anand, A., Oren, D. A., Heninger, G. R., Charney, D. S., Krystal, J. H., 2000. Antidepressant effects of ketamine in depressed patients. Biol Psychiatry 47, 351-354.

Bianchi, M., Baulieu, E. E., 2012. 3beta-Methoxy-pregnenolone (MAP4343) as an innovative therapeutic approach for depressive disorders. Proc Natl Acad Sci USA 109, 1713-1718.

Carr, G. V., Bangasser, D. A., Bethea, T., Young, M., Valentino, R. J., Lucki, I., 2010. Antidepressant-like effects of kappa-opioid receptor antagonists in Wistar Kyoto rats. Neuropsychopharmacology 35, 752-763.

Cominski, T. P., Jiao, X., Catuzzi, J. E., Stewart, A. L., Pang, K. C., 2014. The role of the hippocampus in avoidance learning and anxiety vulnerability. Front Behav Neurosci 8, 273.

Druss B G, Rosenheck R A, Sledge W H. Health and disability costs of depressive illness in a major U.S. corporation. Am J Psychiatry. 2000 August; 157(8):1274-8.

Dugovic, C., Solberg, L. C., Redei, E., Van Reeth, O., Turek, F. W., 2000. Sleep in the Wistar-Kyoto rat, a putative genetic animal model for depression. Neuroreport 11, 627-631.

Durand, M., Berton, O., Aguerre, S., Edno, L., Combourieu, I., Mormede, P., Chaouloff, F., 1999. Effects of repeated fluoxetine on anxiety-related behaviours, central serotonergic systems, and the corticotropic axis in SHR and WKY rats. Neuropharmacology 38, 893-907.

Durand, M., Mormede, P., Chaouloff, F., 2003. Wistar-Kyoto rats are sensitive to the hypolocomotor and anxiogenic effects of mCPP. Behav Pharmacol 14, 173-177.

Fava M, Davidson K G. Definition and epidemiology of treatment-resistant depression. Psychiatr Clin North Am. 1996 June; 19(2):179-200.

Ennaceur A, Delacour J (1988) A new one-trial test for neurobiological studies of memory in rats. 1: Behavioral data. Behavioural brain research 31:47-59.

Ferguson, S. A., Cada, A. M., 2003. A longitudinal study of short- and long-term activity levels in male and female spontaneously hypertensive, Wistar-Kyoto, and Sprague-Dawley rats. Behav Neurosci 117, 271-282.

Ferguson, S. A., Gray, E. P., Cada, A. M., 2003. Early behavioral development in the spontaneously hypertensive rat: a comparison with the Wistar-Kyoto and Sprague-Dawley strains. Behav Neurosci 117, 263-270.

Fontaine-Lenoir, V., Chambraud, B., Fellous, A., David, S., Duchossoy, Y., Baulieu, E. E., Robel, P., 2006. Microtubule-associated protein 2 (MAP2) is a neurosteroid receptor. Proc Natl Acad Sci USA 103, 4711-4716.

Garcia, L. S., Comim, C. M., Valvassori, S. S., Reus, G. Z., Barbosa, L. M., Andreazza, A. C., Stertz, L., Fries, G. R., Gavioli, E. C., Kapczinski, F., Quevedo, J., 2008. Acute administration of ketamine induces antidepressant-like effects in the forced swimming test and increases BDNF levels in the rat hippocampus. Prog Neuropsychopharmacol Biol Psychiatry 32, 140-144.

Greden J F. The burden of disease for treatment-resistant depression. J Clin Psychiatry. 2001; 62 Suppl 16:26-31.

Greenberg P E, Stiglin L E, Finkelstein S N, Berndt E R. The economic burden of depression in 1990. J Clin Psychiatry. 1993 November; 54(11):405-18.

Griebel, G., Cohen, C., Perrault, G., Sanger, D. J., 1999. Behavioral effects of acute and chronic fluoxetine in Wistar-Kyoto rats. Physiol Behav 67, 315-320.

Griebel, G., Cohen, C., Perrault, G., Sanger, D. J., 1999. Behavioral effects of acute and chronic fluoxetine in Wistar-Kyoto rats. Physiol Behav 67, 315-320.

Hauser, S. R., Getachew, B., Taylor, R. E., Tizabi, Y., 2011. Alcohol induced depressive-like behavior is associated with a reduction in hippocampal BDNF. Pharmacol Biochem Behav 100, 253-258.

Jiao, X., Beck, K. D., Pang, K. C. H., Servatius, R. J., 2011. Animal Models of anxiety vulnerability—The Wistar Kyoto rat. In: Selek, S., (Ed), Different Views of Anxiety Disorders. INTECH Open Access Publisher, pp. 95-120.

KESSLER R C, BERGLUND P, DEMLER O, JIN R, KORETZ D, MERIKANGAS K R, RUSH A J; WALTERS E E, WANG P S. The Epidemiology of Major Depressive Disorder: Results From the National Comorbidity Survey Replication (NCS-R). JAMA. 2003; 289: 3095-3105.

LITTLE A. Treatment-resistant depression. Am Fam Physician. 2009 Jul. 15; 80(2): 167-72.

Lopez-Rubalcava, C., Lucki, I., 2000. Strain differences in the behavioral effects of antidepressant drugs in the rat forced swimming test. Neuropsychopharmacology 22, 191-199.

Lopez-Rubalcava, C., Lucki, I., 2000. Strain differences in the behavioral effects of antidepressant drugs in the rat forced swimming test. Neuropsychopharmacology 22, 191-199.

Malkesman, O., Braw, Y., Weller, A., 2007. Assessment of antidepressant and anxiolytic properties of NK1 antagonists and substance P in Wistar Kyoto rats. Physiol Behav 90, 619-625.

Murakami, K., Fellous, A., Baulieu, E. E., Robel, P., 2000. Pregnenolone binds to microtubule-associated protein 2 and stimulates microtubule assembly. Proc Natl Acad Sci USA 97, 3579-3584.

Okamoto, K., Aoki, K., 1963. Development of a strain of spontaneously hypertensive rats. Jpn Circ J 27, 282-293.

Pare, W. P., 1994. Open field, learned helplessness, conditioned defensive burying, and forced-swim tests in WKY rats. Physiol Behav 55, 433-439.

Pare, W. P., 1994. Open field, learned helplessness, conditioned defensive burying, and forced-swim tests in WKY rats. Physiol Behav 55, 433-439.

Pare, W. P., Kluczynski, J., 1997. Differences in the stress response of Wistar-Kyoto (WKY) rats from different vendors. Physiol Behav 62, 643-648.

Pare, W. P., Redei, E., 1993. Depressive behavior and stress ulcer in Wistar Kyoto rats. J Physiol Paris 87, 229-238.

Pare, W. P., Redei, E., 1993. Depressive behavior and stress ulcer in Wistar Kyoto rats. J Physiol Paris 87, 229-238.

Paresys, L., Hoffmann, K., Froger, N., Bianchi, M., Villey, I., Baulieu, E. E., Fuchs, E., 2015. Effects of the Synthetic Neurosteroid: 3beta-Methoxypregnenolone (MAP4343) on Behavioral and Physiological Alterations Provoked by Chronic Psychosocial Stress in Tree Shrews. Int J Neuropsychopharmacol.

Pollier, F., Sarre, S., Aguerre, S., Ebinger, G., Mormede, P., Michotte, Y., Chaouloff, F., 2000. Serotonin reuptake inhibition by citalopram in rat strains differing for their emotionality. Neuropsychopharmacology 22, 64-76.

RUSH A J, WARDEN D, WISNIEWSKI S R, FAVA M, TRIVEDI M H, GAYNES B N, NIERENBERG A A. STAR*D: revising conventional wisdom. CNS Drugs. 2009 Aug. 1; 23(8):627-47.

Scheuing, L., Chiu, C. T., Liao, H. M., Chuang, D. M., 2015. Antidepressant mechanism of ketamine: perspective from preclinical studies. Front Neurosci 9, 249.

Scholl, J. L., Renner, K. J., Forster, G. L., Tejani-Butt, S., 2010. Central monoamine levels differ between rat strains used in studies of depressive behavior. Brain Res 1355, 41-51.

Tejani-Butt, S., Kluczynski, J., Pare, W. P., 2003. Strain-dependent modification of behavior following antidepressant treatment. Prog Neuropsychopharmacol Biol Psychiatry 27, 7-14.

Thase M E, Rush A J. When at first you don't succeed: sequential strategies for antidepressant non-responders. J Clin Psychiatry. 1997; 58 Suppl 13:23-9.

Tizabi, Y., Bhatti, B. H., Manaye, K. F., Das, J. R., Akinfiresoye, L., 2012. Antidepressant-like effects of low ketamine dose is associated with increased hippocampal AMPA/NMDA receptor density ratio in female Wistar-Kyoto rats. Neuroscience 213, 72-80.

TRIVEDI M H, FAVA M, MARANGELL L B, OSSER D N, SHELTON R C. Use of treatment algorithms for depression. Prim Care Companion J Clin Psychiatry 2006; 8(5):291-8.

TRIVEDI M H, RUSH A J, CRISMON M L, KASHNER T M, TOPRAC M G, CARMODY T J, KEY T, BIGGS M M, SHORES-WILSON K, WITTE B, SUPPES T, MILLER A L, ALTSHULER K Z, SHON S P. Clinical results for patients with major depressive disorder in the Texas Medication Algorithm Project. Arch Gen Psychiatry. 2004 July; 61(7):669-80.

U.S. Pat. No. 8,334,278

West, M. J. (1999). Stereological methods for estimating the total number of neurons and synapses: issues of precision and bias. 331-339.

Will, C. C., Aird, F., Redei, E. E., 2003. Selectively bred Wistar-Kyoto rats: an animal model of depression and hyper-responsiveness to antidepressants. Mol Psychiatry 8, 925-932.

Willne P, Belzung C, Scheel-Kruger J (2014) Resistance to antidepressant drugs: the case for a more predisposition-based and less hippocampocentric research paradigm. Behav Pharmacol 25:352-371.

Willner, P., Belzung, C., 2015. Treatment-resistant depression: are animal models of depression fit for purpose? Psychopharmacology (Berl) 232, 3473-3495.

WO2004067010A1

Yilmaz, A., Schulz, D., Aksoy, A., Canbeyli, R., 2002. Prolonged effect of an anesthetic dose of ketamine on behavioral despair. Pharmacol Biochem Behav 71, 341-344.

Zarate, C. A., Jr., Singh, J. B., Carlson, P. J., Brutsche, N. E., Ameli, R., Luckenbaugh, D. A., Charney, D. S., Manji, H. K., 2006. A randomized trial of an N-methyl-D-aspartate antagonist in treatment-resistant major depression. Arch Gen Psychiatry 63, 856-864.

The invention claimed is:

1. A method for treating treatment-resistant depression (TRD) in a subject in need thereof, comprising administering to said patient a therapeutically efficient amount of 3β-methoxy-pregna-5α-ene-20α-one of formula:

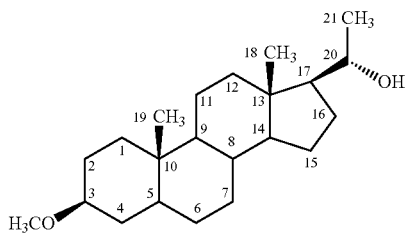 [SMILES: CO[C@H]1CC[C@@]2(C)C(CCC3C2CC[C@@]2(C)C3CC[C@@H]2[C@H](C)O)C1]

or a pharmaceutically acceptable salt thereof;
wherein TRD is a major depressive disorder that does not respond to, or does not evolve favorably under the influence of, adequate doses and duration of treatment with at least one anti-depressant, wherein the anti-depressant is a selective serotonin reuptake inhibitor (SSRI).

2. The method according to claim 1, wherein said compound is intended for use at a dose of 50 to 2000 mg/day.

3. The method according to claim 1, wherein said compound is intended for use in depressive patients in which at least two successive treatments with antidepressant drugs of different pharmacological classes have failed (stage 2 of Thase and Rush classification of treatment-resistant depression).

* * * * *

UNITED STATES PATENT AND TRADEMARK OFFICE
CERTIFICATE OF CORRECTION

| | |
|---|---|
| PATENT NO. | : 9,943,528 B2 |
| APPLICATION NO. | : 15/444778 |
| DATED | : April 17, 2018 |
| INVENTOR(S) | : Massimiliano Bianchi, Etienne Baulieu and Isabelle Villey |

It is certified that error appears in the above-identified patent and that said Letters Patent is hereby corrected as shown below:

In the Claims

Column 36, Lines 20-30, the chemical drawing:

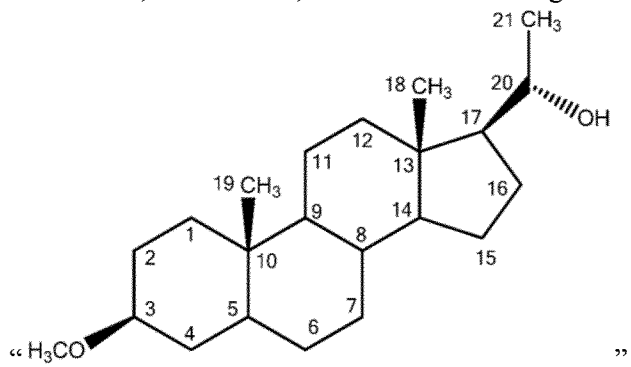

Should read:

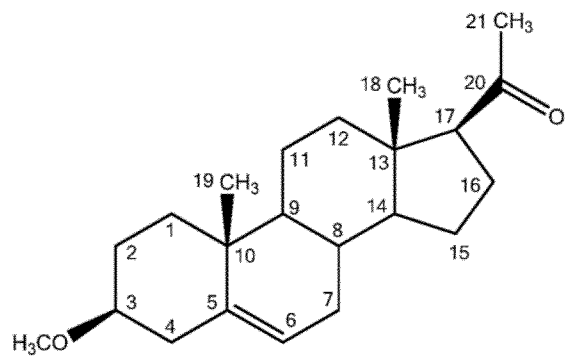

Signed and Sealed this
Seventeenth Day of September, 2019

Andrei Iancu
*Director of the United States Patent and Trademark Office*